(12) United States Patent
Fradet et al.

(10) Patent No.: US 11,104,958 B2
(45) Date of Patent: *Aug. 31, 2021

(54) METHOD TO DETECT PROSTATE CANCER IN A SAMPLE

(71) Applicant: Gen-Probe Incorporated, San Diego, CA (US)

(72) Inventors: Yves Fradet, Quebec (CA); Camille Chypre, Annecy (FR); Lyson Piche, Quebec (CA); Genevieve Garon, Quebec (CA)

(73) Assignee: GEN-PROBE INCORPORATED, San Diego, CA (US)

( * ) Notice: Subject to any disclaimer, the term of this patent is extended or adjusted under 35 U.S.C. 154(b) by 346 days.

This patent is subject to a terminal disclaimer.

(21) Appl. No.: 16/014,697

(22) Filed: Jun. 21, 2018

(65) Prior Publication Data
US 2018/0363064 A1 Dec. 20, 2018

Related U.S. Application Data

(60) Division of application No. 15/093,214, filed on Apr. 7, 2016, now Pat. No. 10,006,092, which is a division of application No. 14/011,988, filed on Aug. 28, 2013, now abandoned, which is a division of application No. 13/470,451, filed on May 14, 2012, now Pat. No. 8,546,551, which is a division of application No. 12/500,749, filed on Jul. 10, 2009, now Pat. No. 8,192,931, which is a continuation of application No. 10/773,440, filed on Feb. 9, 2004, now abandoned.

(60) Provisional application No. 60/445,436, filed on Feb. 7, 2003.

(51) Int. Cl.
C12Q 1/6886 (2018.01)

(52) U.S. Cl.
CPC ..... *C12Q 1/6886* (2013.01); *C12Q 2600/158* (2013.01); *C12Q 2600/16* (2013.01)

(58) Field of Classification Search
CPC .................................................. C12Q 1/6886
USPC ....................................................... 536/23.1
See application file for complete search history.

(56) References Cited

U.S. PATENT DOCUMENTS

| | | | |
|---|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,851,331 A | 7/1989 | Vary |
| 4,965,188 A | 10/1990 | Mullis et al. |
| 5,002,867 A | 3/1991 | Macevicz |
| 5,068,176 A | 11/1991 | Vijg et al. |
| 5,082,670 A | 1/1992 | Gage et al. |
| 5,112,736 A | 5/1992 | Caldwell et al. |
| 5,118,801 A | 6/1992 | Lizardi |
| 5,149,625 A | 9/1992 | Church et al. |
| 5,174,986 A | 12/1992 | Berns et al. |
| 5,175,383 A | 12/1992 | Leder et al. |
| 5,183,949 A | 2/1993 | Kindt et al. |
| 5,202,231 A | 4/1993 | Drmanac et al. |
| 5,219,989 A | 6/1993 | Sonenberg et al. |
| 5,283,174 A | 2/1994 | Arnold, Jr. et al. |
| 5,312,728 A | 5/1994 | Lizardi et al. |
| 5,399,491 A | 3/1995 | Kacian et al. |
| 5,422,252 A | 6/1995 | Walker et al. |
| 5,466,590 A | 11/1995 | Sariaslani et al. |
| 5,503,980 A | 4/1996 | Cantor |
| 5,547,842 A | 8/1996 | Hogan et al. |
| 5,554,516 A | 9/1996 | Kaclan et al. |
| 5,585,481 A | 12/1996 | Arnold, Jr. et al. |
| 5,593,974 A | 1/1997 | Rosenberg et al. |
| 5,639,604 A | 6/1997 | Arnold, Jr. et al. |
| 5,656,207 A | 8/1997 | Woodhead et al. |
| 5,658,737 A | 8/1997 | Nelson et al. |
| 5,674,682 A | 10/1997 | Croce et al. |
| 5,773,705 A | 6/1998 | Vierstra et al. |
| 5,837,832 A | 11/1998 | Chee et al. |
| 5,861,242 A | 1/1999 | Chee et al. |
| 5,925,517 A | 7/1999 | Tyagi et al. |
| 5,939,258 A | 8/1999 | Croce et al. |

(Continued)

FOREIGN PATENT DOCUMENTS

| | | |
|---|---|---|
| EP | 0125023 | 11/1984 |
| EP | 0160228 | 11/1985 |

(Continued)

OTHER PUBLICATIONS

Altschul, S.F., et al., "Gapped BLAST and PSI-BLAST: a new generation of protein database search programs," Nucl. Acids Res. 25:3389-3402 (1997).

(Continued)

*Primary Examiner* — Sean E Aeder
(74) *Attorney, Agent, or Firm* — McNeill Baur PLLC; Michael J. Gilly

(57) ABSTRACT

The present invention provides methods to detect prostate cancer by detecting the RNA encoded by PCA3. The disclosure provides a method for determining a predisposition, or presence of prostate cancer comprising: (a) contacting a sample with at least one oligonucleotide that hybridizes to a PCA3 polynucleotide; (b) detecting an amount of PCA3 and second prostate-specific polynucleotides; and (c) comparing the amount of PCA3 polynucleotide that hybridizes to the oligonucleotide to a predetermined cut off value, and determining the presence or absence of prostate cancer. Diagnostic kits are provided for detecting prostate cancer or the risk of developing same comprising: (a) at least one container means containing at least one oligonucleotide probe or primer that hybridizes to PCA3 (b) at least one oligonucleotide probe or primer that hybridizes with a second prostate specific nucleic acid; and (c) reagents for detecting PCA3 and the second prostate specific nucleic acid.

20 Claims, 4 Drawing Sheets

Specification includes a Sequence Listing.

(56) References Cited

U.S. PATENT DOCUMENTS

| | | | |
|---|---|---|---|
| 6,037,130 A | 3/2000 | Tyagi et al. | |
| 6,087,133 A | 7/2000 | Dattagupta et al. | |
| 6,110,678 A | 8/2000 | Weisburg et al. | |
| 6,261,562 B1 | 7/2001 | Xu et al. | |
| 6,262,245 B1 | 7/2001 | Xu et al. | |
| 6,280,952 B1 | 8/2001 | Weisburg et al. | |
| 6,287,820 B1 | 9/2001 | Umansky et al. | |
| 6,383,739 B1 | 5/2002 | Kurth et al. | |
| 6,395,278 B1 | 5/2002 | Xu et al. | |
| 6,465,611 B1 | 10/2002 | Xu et al. | |
| 6,479,263 B1 | 11/2002 | Slawin et al. | |
| 6,528,260 B1 | 3/2003 | Blumenfeld et al. | |
| 6,534,273 B2 | 3/2003 | Weisburg et al. | |
| 6,551,778 B1 | 4/2003 | Harvey et al. | |
| 6,800,746 B2 | 10/2004 | Xu et al. | |
| 6,897,024 B2 | 5/2005 | Bussemakers et al. | |
| 7,008,765 B1 | 3/2006 | Bussemakers et al. | |
| 7,138,235 B2 | 11/2006 | Bussemakers et al. | |
| 7,368,545 B1 | 5/2008 | Busse et al. | |
| 7,632,643 B2 | 12/2009 | Bussemakers et al. | |
| 7,655,408 B2 | 2/2010 | Busse et al. | |
| 7,927,806 B2 | 4/2011 | Busse et al. | |
| 8,192,931 B2 | 6/2012 | Fradet et al. | |
| 8,241,848 B2 | 8/2012 | Busse et al. | |
| 8,546,551 B2 | 10/2013 | Fradet et al. | |
| 10,006,092 B2 | 6/2018 | Fradet et al. | |
| 10,752,957 B2 * | 8/2020 | Hessels | C12Q 1/6886 |
| 2002/0022248 A1 | 2/2002 | Xu et al. | |
| 2002/0035244 A1 | 3/2002 | Cohen et al. | |
| 2002/0168638 A1 | 11/2002 | Schlegel et al. | |
| 2003/0165850 A1 | 9/2003 | Bussemakers et al. | |
| 2005/0158792 A1 | 7/2005 | Bussemakers et al. | |
| 2005/0164223 A1 | 7/2005 | Schalken et al. | |
| 2005/0282170 A1 | 12/2005 | Fradet et al. | |
| 2006/0099658 A1 | 5/2006 | Bussemakers et al. | |
| 2008/0261228 A1 | 10/2008 | Busse et al. | |
| 2010/0021884 A1 | 1/2010 | Hessels et al. | |
| 2011/0165573 A1 | 7/2011 | Fradet et al. | |
| 2012/0309001 A1 | 2/2012 | Fradet et al. | |
| 2013/0344487 A1 | 12/2013 | Fradet et al. | |
| 2016/0281174 A1 | 9/2016 | Fradet et al. | |

FOREIGN PATENT DOCUMENTS

| | | |
|---|---|---|
| EP | 0171496 | 2/1986 |
| EP | 0173494 | 5/1986 |
| EP | 0184187 | 11/1986 |
| EP | 0256932 | 2/1988 |
| EP | 0520794 | 12/1992 |
| EP | 0320308 | 3/1993 |
| EP | 0747706 | 12/1996 |
| EP | 1295125 | 5/2006 |
| WO | WO 86/01533 | 3/1986 |
| WO | WO 87/02671 | 10/1986 |
| WO | WO 90/00944 | 2/1990 |
| WO | WO 91/19008 | 12/1991 |
| WO | WO 93/03743 | 4/1993 |
| WO | WO 93/08845 | 5/1993 |
| WO | WO 93/13121 | 7/1993 |
| WO | WO 94/09820 | 5/1994 |
| WO | WO 94/15646 | 7/1994 |
| WO | WO 95/28498 | 10/1995 |
| WO | WO 95/32305 | 11/1995 |
| WO | WO 96/11266 | 4/1996 |
| WO | WO 96/14875 | 5/1996 |
| WO | WO 96/32966 | 10/1996 |
| WO | WO 98/02582 | 1/1998 |
| WO | WO 98/45420 | 10/1998 |
| WO | WO 00/04149 | 1/2000 |
| WO | WO 00/50899 | 8/2000 |
| WO | WO 00/58470 | 10/2000 |
| WO | WO 01/23550 | 4/2001 |
| WO | WO 01/25272 | 4/2001 |
| WO | WO 01/25273 | 4/2001 |
| WO | WO 01/34802 | 5/2001 |
| WO | WO 01/44507 | 6/2001 |
| WO | WO 01/51633 | 7/2001 |
| WO | PCT/CA00/01154 | 8/2001 |
| WO | WO 01/60860 | 8/2001 |
| WO | WO 01/73032 | 10/2001 |
| WO | WO 02/24718 | 3/2002 |
| WO | WO 02/30268 | 4/2002 |
| WO | PCT/CA00/01154 | 8/2002 |
| WO | PCT/CA04/000170 | 8/2004 |
| WO | WO 2004/070056 | 8/2004 |
| WO | PCT/EP05/014021 | 8/2006 |

OTHER PUBLICATIONS

Armbruster et al., "Enzyme immunoassay, kinetic microparticle immunoassay, radioimmunoassay, and fluorescence polarization immunoassay compared for drugs-of-abuse screening", Clin Chem. 39(10):2137-46 (1993).

Arnold, Jr., L.J., et al., "Assay Formats Involving Acridinium-Ester-Labe/ed DNA Probes," Clin. Chem. 35:1588-1594 (1989).

Auffray C, Rougeon F. "Purification of mouse immunoglobulin heavy-chain messenger RNAs from total myeloma tumor RNA". Eur J Biochem 1980;107:303-14.

Barbu V, Dautry F. "Northern blot normalization with a 28S rRNA oligonucleotide probe". Nucleic Acids Res 1989;17:7115.

Beduschi MC, Oesterling JE. "Percent free prostate-specific antigen: the next frontier in prostate-specific antigen testing". Urology 51:98-109 (1998).

Bernard PS, Wittwer CT. "Real-time PCR technology for cancer diagnostics". Clin. Chem. 48:1178-85 (2002).

Black, D.L., "Mechanisms of Alternative Pre-Messenger RNA Splicing," Annu. Rev. Biochem. 72:291-336 (Feb. 2003).

Boom, R., et al., "Rapid and Simple Method for Purification of Nucleic Acids," J. Clin, Microbiol. 28:495-503 (1990).

Boulikas, T., "Gene Therapy of Prostate Cancer: p53, Suicidal Genes, and Other Targets," Anticancer Res. 17:1471-1505 (1997).

Bowie, J.U., "Deciphering the Message in Protein Sequences: Tolerance to Amino Acid Substitutions," Science 247:1306-1311 (1990).

Brakebusch, C., et al., "Expression of the 90K Immunostimulator Gene Is Controlled by a Promoter with Unique Features," J. Biol. Chem. 272:3674-3682 (1997).

Brawer et al., "Screening for prostatic carcinoma with prostate specific antigen". J Urol 147:841-5 (1992).

Brawer MK. "Prostate-specific antigen". Semin Surg Oncol. 18:3-9 (2000).

Brinster et al., "Factors affecting the efficiency of introducing foreign DNA into mice by microinjecting eggs", PNAS. 82(13):4438-4442 (1985).

Brown, A.M., "A step-by-step guide to non-linear regression analysis of experimental data using a Microsoft Excel spreadsheet," Comput. Methods Programs Biomed. 65:191-200 (Jun. 2001).

Buck, G.A., et al., "Design Strategies and Performance of Custom DNA Sequencing Primers," BioTechniques 27:528-536 (Sep. 1999).

Burgess, W.H., et al., "Possible Dissociation of the Heparin-binding and Mitogenic Activities of Heparin-binding (Acidic Fibroblast) Growth Factor-1 from its Receptorbinding Activities by Site-directed Mutagenesis of a Single Lysine Residue," J Cell. Biol. 111:2129-2138 (1990).

Bussemakers et al., "DD3: a new prostate-specific gene, highly overexpressed in prostate cancer", Cancer Research, 59:5975-9 (1999).

Bussemakers, M.J.G., et al., "DD3: a new prostate specific marker, overexpressed in prostatic tumors," Proc. Annu. Meet. Amer. Assoc. Cancer Res. 87:515, Abstract No. 3522, 87th Annual meeting of the American Association for Cancer Research (1996).

Bussemakers, M.J., and Isaacs, W.B., "Identification of Genes Associated with Prostate Cancer Development," Urol. Res. 21:452, Abstract No. P42 (1993).

Bussemakers, M.J.G., "Changes in Gene Expression and Targets for Therapy," Eur. Urol. 35:408-412 (Jan. 1999).

(56) References Cited

OTHER PUBLICATIONS

Bussemakers, M.J.G., et al., "Assessment of the Clincial Usefulness of the Prostate-Cancer-Specific DD3 Gene," Eur. Urol. 36: 508, Abstract No. 0139 (Nov. 1999).
Bussemakers, M.J.G., et al., "DD3: A New Prostate Specific Marker, Overexpressed in Prostatic Tumors," Presented at Breast and Prostate Cancer: Basic Mechanisms, Taos, New Mexico, Abstract No. 102, 1 page (Jan. 29-Feb. 4, 1996).
Bussemakers, M.J.G., et al., "DD3: A New Prostate Specific Marker, Overexpressed in Prostatic Tumors," Presented at Meeting for the Dutch Association for Tumor Cell Biology, May, The Netherlands, 1 page (1996).
Bussemakers, M.J.G., et al., "DD3: A New Prostate-Specific Marker, Strongly Overexpressed in Prostatic Tumors," Urol. Res. 25:76, Abstract No. 02.2 (1997).
Bussemakers, M.J.G., et al., "Identification of DD3: A New Gene Overexpressed in Prostatic Tumors," Urol. Res. 23:253, Abstract No. 0 36 (1995).
Bussemakers, MJ.G., and Isaacs, W.B., "Identification of Genes Associated with Prostate Cancer Development," Presented at 8th Annual Spring Meeting, May 13-May 14, San Fransico, CA, one page, Society for Basic Urologic Research (1994).
Bussemakers, MJ.G., et al., "DD3: A New Prostate Specific Marker, Overexpressed in Prostatic Tumors," Presented at Fall Symposium, Dec. 7-10, Chapel Hill, North Carolina, 1 page, Society for Basic Urologic Research (1995).
Bustin SA. "Absolute quantification of mRNA using real-time reverse transcription polymerase chain reaction assays", J Mol Endocrinol 2000;25:169-93.
Cairns, P., et al., "Molecular Detection of Prostate Cancer in Urine by GSTP1 Hypermethylation," Clin. Cancer Res. 7:2727-2730 (Sep. 2001).
Catalona et al., "Measurement of prostate-specific antigen in serum as a screening test for prostate cancer". N Engl J Med, 324:1156-61 (1991).
Cheung, R.C., et al., "Rapid and Sensitive Method for Detection of Hepatitis C Virus RNA by Using Silica Particles," J. Clin. Microbiol. 10:2593-2597 (1994).
Chitale and Khubchandani, "Interpretation of Prostatic Biopsies: A Review", The Internet Journal of Urology. 3(1), (2005).
Clements, J.A., et al., "Molecular Detection of Prostate Cells in Ejaculate and Urethral Washings in Men With Suspected Prostate Cancer," J. Urol. 161:1337-1343 (Apr. 1999).
Cleutjens, K.B.J.M., et al., "A 6-kb Promoter Fragment Mimics in Transgenic Mice the Prostate-Specific and Androgen-Regulated Expression of the Endogenous Prostate-Specific Antigen Gene in Humans," Mol. Endocrinol. I 1:1256-1265 (1997).
Cleutjens, K.B.J.M., et al., "An Androgen Response Element in a Far Upstream Enhancer Region Is Essential for High, Androgen-Regulated Activity of the Prostate-Specific Antigen Promoter," Mol. Endocrinol. 11:148-161 (1997).
Database EMBL Online, Bussemakers et al., Accession No. AF103908 (Nov. 1999).
Database NCBI Entrez, GenBank Report, Accession No. AL359314 (May 2001).
Database NCBI, Accession No. AF103907 (Aug. 2000).
Database NCBI, Accession No. AF103908 (Aug. 2000).
De Kok et al., "DD3(PCA3), a very sensitive and specific marker to detect prostate tumors." Cancer Res. 62:2695-8 (2002).
Deras et al., "PCA3: A molecular urine assay for preicting prostate biopsy outcome", J Urol 179:1587-1592 (2008).
Dieffenbach et al., "General concepts for PCR primer design", PCR Methods Appl. 3:30-37 (1993).
Edery, I., et al., "High-level synthesis in *Escherichia coli* of functional cap-binding eukaryotic initiation factor elF-4E and affinity purification using a simplified cap-analog resin," Gene 74:517-525 (1988).
El-Shirbiny, A.M., "Prostatic Specific Antigen," Adv. Clinical Chem. 31:99-133 (1994).

Ferrari AC, Stone NN, Eyler JN, Gao M, Mandeli J, Unger P et al. Prospective analysis of prostate-specific markers in pelvic lymph nodes of patients with high risk prostate cancer. J Natl Cancer Inst 1997;89:1498-504.
File History for U.S. Appl. No. 10/773,440, filed Feb. 9, 2004.
File History for U.S. Appl. No. 12/500,749, filed Jul. 10, 2009.
File History for U.S. Appl. No. 13/470,451, filed May 14, 2012.
File History for U.S. Appl. No. 14/011,988, filed Aug. 28, 2013.
File History for U.S. Appl. No. 15/093,214, filed Apr. 7, 2016.
Gandini et al., "Is DD3 a New Prostate-Specific Gene?," Anticancer Res. 23:305-308 (Jan.-Feb. 2003).
Gen-Probe Brochure, "Prostate Cancer Gene 3 (PCA3): the new tool available to improve the diagnosis of prostate cancer in a simple urine test", Gen_Probe Incorporated (2007).
Gibson et al., "A novel method for real time quantitative RT-PCR". Genome Res. 6:995-1001 (1996).
Goessl et al, "DNA-Based Detection of Prostate Cancer in Blood, Urine, and Ejaculates," Ann NY Acad. Sci. 945: 51-58, (2001).
Goessl et al., "A DNA-Based Method for Detection of Prostate Cancer Cells in Urine After Prostatic Massage," Eur. Urol. Suppl. 1:32, article 118 (Jan. 2002).
Goessl et al., "DNA-Based Detection of Prostate Cancer in Urine After Prostatic Massage," Urology 58:335-338 (Sep. 2001).
Goessl et al., "Fluorescent Methylation-specific Polymerase Chain Reaction for DNA-based Detection of Prostate Cancer in Bodily Fluids," Cancer Res. 60:5941-5945 (Nov. 2000).
Goldman et al., "Can prostate-specific antigen reverse transcriptase-polymerase chain reaction be used as a prospective test to diagnose prostate cancer?" World J Urol. 15:257-61 (1997).
Gomella et al., "Reverse Transcriptase Polymerase Chain Reaction for Prostate Specific Antigen in the Management of Prostate Cancer," J. Urology 158:326-337 (1997).
Gotoh, A., et al., "Development of Prostate-Specific Antigen Promoter-Based Gene Therapy for Androgen-Independent Human Prostate Cancer," J. Urol. 160:220-229 (Jul. 1998).
Grasso et al., "Combined nested RT-PCR assay for prostate-specific antigen and prostate-specific membrane antigen in prostate cancer patients: correlation with pathological stage". Cancer Res. 58:1456-9 (1998).
Grayburn and Sims, "Anchored Oligo(dT) Primers for Automated Dye Terminator DNA Sequencing", BioTechniques. 25(3):340-346 (1998).
Groskopf et al., "APTIMA PCA3 Molecular Urine Test: Development of a Method to Aid in the Diagnosis of Prostate Cancer," Clin. Chem. 52: 1089-1095, (2006).
Gu et al., "Prostate stem cell antigen (PSCA) expression increases with high gleason score, advanced stage and bone metastasis in prostate cancer". Oncogene. 19:1288-96 (2000).
Guichet et al., "The nuclear receptor homologue Ftz-F1 and the homeodomain protein Ftz are mutually dependent cofactors," Nature 385:548-552 (1997).
Hessels, D., et al. "DD3Pcm-based Molecular Urine Analysis for the Diagnosis of Prostate Cancer," Eur. Urol. 44:8-15 (Jul. 2003).
Hillier and Green, "OSP: A computer program for choosing PCR and DNA sequenceing primers", PCR Methods Appl. 1:124-128 (1991).
Horninger et al., "Complexed prostate-specific antigen for early detection of prostate cancer in men with serum prostate-specific antigen levels of 2 to 4 nanograms per milliliter." Urology. 60(4):31-35 (2002).
Houdebine, L-M., "Production of pharmaceutical proteins from transgenic animals," J. Biochern. 34:269-287 (1994).
Hsing, A.W., et al., "International Trends and Patterns of Prostate Cancer Incidence and Mortality," Int J. Cancer 85:60-67 (Jan. 2000).
Ingelfinger, R.J., "Nephrogenic Adenomas As Renal Tubular Outposts," N. Engl. J. Med. 347:684-686 (Aug. 2002).
Israeli et al., "Sensitive Nested Reverse Transcription Polymerase Chain Reaction Detection of Circulating Prostatic Tumor Cells: Comparison of Prostate-specific Membrane Antigen and Prostatespecific Antigen-based Assays," Cancer Res. 54:6306-6310 (1994).

(56) References Cited

OTHER PUBLICATIONS

Iwakiri, J., et al., "An Analysis of Urinary Prostate Specific Antigen Before and After Radical Prostatectomy: Evidence for Secretion of Prostate Specific Antigen by the Periurethral Glands," J. Urol. 149:783-786 (1993).
Jensen et al., "Cancer in the European Community and its member states". Eur J Cancer 26:1167-256 (1990).
Journal Sentinel wire reports, "Prostate blood test may but down on biopsies", May 20, 1998.
Kamoi K, Babaian RJ. "Advances in the application of prostate-specific antigen in the detection of early-stage prostate cancer". Semin Oncol, 26:140-9 (1999).
Katz et al., "Enhanced reverse transcriptase-polymerase chain reaction for prostate specific antigen as an indicator of true pathologic stage in patients with prostate cancer". Cancer. 75:1642-8 (1995).
Katz et al., "Molecular staging of prostate cancer with the use of an enhanced reverse transcriptase-PCR assay". Urology 1994;43:765-75.
Kirby, R.S., "Pre-treatment staging of prostate cancer: recent advances and future prospects," Prostate Cancer and Prostatic Dis. 1:2-10 (1997).
Kwoh, D.Y., et al., "Transcription-based amplification system and detection of amplified human immunodeficiency virus type 1 with a bead-based sandwich hybridization format," Proc. Natl. Acad. Sci. USA. 86:1173-1177 (1989).
Kwok et al., "A guide to the design and use of mismatched and degenerate primers", PCR Methods Appl. 3:39-47 (1994).
Landis et al., "Cancer Statistics, 1998", CA Cancer J Clin 48(1):6-29 (1998).
Landis et al., "Cancer Statistics, 1999," CA Cancer J. Clin. 49:8-31 (Jan.-Feb. 1999).
Lange, P.H., "Chapter 41. Tumor Markers in Prostate Cancer," in: Principles and Practice of Genitourinary Oncology, Raghaven, D. et al., eds., Lippincott-Raven Publishers, Philadelphia, PA, pp. 417-425 (1997).
Lathe, R., "Synthetic Oligonucleotide Probes Deduced from Amino Acid Sequence Data Theoretical and Practical Considerations," J. Mol. Biol. 183:1-12 (1985).
Lazar, E., et al., "Transforming growth factor a: mutation of aspartic acid 47 and leucine 48 results in different biological activities," Mol. Cell Biol. 8:1247-1252 (1988).
Letran, J.L. et al., "Repeat Ultrasound Guided Prostate Needle Biopsy: Use of Free-To-Total Prostate Specific Antigen Ratio in Predicting Prostatic Carcinoma," J. Urology 160:426-429 (Aug. 1998).
Lin et al., "Prostatelocalized and androgen-regulated expression of the membrane-bound serine protease TMPRSS2". Cancer Res. 59:4180-4 (1999).
Lintula S, Stenman UH. "The expression of prostate-specific membrane antigen in peripheral blood leukocytes". J Urol. 157:1969-72 (1997).
Lizardi, P., et al., "Exponential Amplification of Recombinant-RNA Hybridization Probes," BioTechnology 6:1197-1202 (1988).
Lowe et al., "A computer program for selection of oligonucleotide primers for polymerase chain reactions", Nucleic Acids Research. 18(7):1757-1761 (1990).
Malek, L., et al., "Nucleic Acid Sequence-Based Amplification (NASBA)," Methods Mol. Biol. 28:253-260 (1994).
Marks et al., "PCA3 molecular urine assay for prostate cancer in men undergoing repeat biopsy", Adult Urology, 69(3):532-535(2007).
Martiniello-Wilks, R., et al.,"In Vivo Gene Therapy for Prostate Cancer: Preclinical Evaluation of Two Different Enzyme-Directed Prodrug Therapy Systems Delivered by Identical Adenovirus Vectors," Hum. Gene Ther. 9:1617-1626 (Jul. 1998).
Matteucci, M.D., and Caruthers, M.H., "Synthesis of Deoxyoligonucleotides on a Polymer Support," J. Am. Chem. Soc. 103:3185-3191 (1981).
Merriam-Webster Online Dictionary, definition for "kit" (Accessed Dec. 2005).

Mettlin et al., "The National Cancer Data Base report on longitudinal observations on prostate cancer". Cancer 77:2162-6 (1996).
Miller, P.S., and Ts'o, P.O.P., "Chapter 30: Oligonucleotide Inhibitors of Gene Expression in Living Cells: New Opportunities in Drug Design," Annu. Rep. Med, Chem. 23:295-304 (1988).
Millikan, R.E., "Chemotherapy of Advanced Prostatic Carcinoma," Semin. Oncol. 26:185-191 (Apr. 1999).
Mintun et al., "Increased lactate pyruvate ratio augments blood flow in physiologically activated human brain", 101(2):659-664 (2004).
Morvan, F., et al., "a-DNA. L Synthesis, characterization by high field III-NMR, and base-pairing properties of the unnatural hexadeoxyribonucleotide a-[d(CpCpTpTpCpC)] with its complement P-[d(GpGpApApGpG)]," Nucleic Acids Res. 14:5019-5035 (1986).
Muller and Brenner, "Urine Markers as Possible Tools for Prostate Cancer Screening: Review of Performance Characteristics and Practicality," Clinical Chemistry 52:562-573 (2006).
Murphy et al., "Evaluation and comparison of two new prostate carcinoma markers. Freeprostate specific antigen and prostate specific membrane antigen". Cancer. 78:809-18 (1996).
Nelson et al., "Molecular cloning and characterization of prostate, an androgen-regulated serine protease with prostate-restricted expression". Proc Natl Acad Sci USA 96:3114-9 (1999).
Nielsen, P.E., "Applications of peptide nucleic acids," Curr. Opin. Biotechnol. 10:71-75 (Feb. 1999).
Nixon RG, Brawer MK. Enhancing the specificity of prostate-specific antigen (PSA): an overview of PSA density, velocity and age-specific reference ranges. Br J Urol 1997;79 Suppl 1:61-7.
Nurmi et al., "High-performance real-time quantitative RT-PCR using lanthanide probes and a dual-temperature hybridization assay". Anal Chem 2002;74:3525-32.
Oettgen et al., "PDEF, a novel prostate epithelium-specific ets transcription factor, interacts with the androgen receptor and activates prostate-specific antigen gene expression". J Biol Chem 275:1216-25 (2000).
Office Action for U.S. Appl. No. 09/996,953, inventors Bussemakers, M.J., et al., filed Nov. 30, 2001, dated Aug. 26, 2003.
Pang, S., et al., "Identification of a Positive Regulatory Element Responsible for Tissue-specific Expression of Prostate-specific Antigen," Cancer Res. 57:495-499 (1997).
Partin et al., "Complexed Prostate Specific Antigen Improves Specificity for Prostate Cancer Detection: Results of a Prospective Multicenter Clinical Trial", Journal of Urology, 170(5):1787-1791 (2003).
Paule MR, White RJ. Survey and summary: transcription by RNA polymerases I and I II. Nucleic Acids Res 2000;28:1283-98.
Polascik et al., "Prostate specific antigen: a decade of discovery—what we have learned and where we are going". J Urol. 62:293-306 (1999).
Quandt, K., et al., "MatInd and MatInspector: new, fast and versatile tools for detection of consensus matches in nucleotide sequence data," Nucl. Acids Res. 23:4878-4884 (1995).
Raeymaekers L. "Quantitative PCR: theoretical considerations with practical implications". Anal Biochem. 214:582-5 (1993).
Rieger-Christ, K., et al., "Identification of Fibroblast Growth Factor Receptor 3 Mutations in Urine Sediment DNA Samples Complements Cytology in Bladder Tumor Detection," Cancer 98:737-744 (Aug. 2003).
Ringsrud, K.M., "Cells in the Urine Sediment," Lab. Med. 32:153-155 (Mar. 2001).
Roobol et al., "Tumour Markers in Prostate Cancer III: Biomarkers in Urine," Acta Oncol., 50: 85-89, (2011).
Rubanyi, G.M., "The future of human gene therapy," Mol. Aspects Med. 22:113-142 (Jun. 2001).
Rubin and Levy, "A mathematical model and a computerized simulation of PCR using complex templates", Nucleic Acids Research, 24(18):3538-3545 (1996).
Rychlik and Rhaods, "A computer program for choosing optimal oligonucleotides for filter hybridization, sequencing and in vitro amplification of DNA", Nucleic Acids Research, 17(21):8543-8551 (1989).

(56) References Cited

OTHER PUBLICATIONS

Rychlik, W, "Chapter 2: Selection of primers for polymerase chain reaction", from Methods in Molecular Biology vol. 15. PCR Protocols: Current methods and applications. Ed. Bruce A, White, Humana Press Inc, pp. 31-40 (1993).

Schalken et al., "New targets for therapy in prostate cancer: Differential display code 2 (DD3(PCA3)), a highly prostate cancer-specific gene", Urology 62(Suppl. 5A):34-43 (2003).

Schalken, J., "Molecular Diagnostics and Therapy of Prostate Cancer: New Avenues," Eur. Urol. 34 Suppl 3:3-6, S. Karger AG (1998).

Schuur, E.R., et al., "Prostate-specific Antigen Expression Is Regulated by an Upstream Enhancer," J. Biol. Chem. 271:7043-7051 (1996).

Schwartz, C.J., et al., "FTZ-Factorl and Fushi tarazu interact via conserved nuclear receptor and coactivator motifs," EMBO J 20:510-519 (Feb. 2001).

Sequence Comparisions in Office Action for U.S. Appl. No. 10/773,440, inventors Fradet, Y. et al., filed Feb. 9, 2004, dated Jun. 23, 2006.

Sharrocks, AD, "Chapter 2: The design of primers for PCR", from PCR Technology Current Innovations. Eds. Hugh G, Griffin and Annette M. Griffin. CRC Press pp. 5-11 (1994).

Sidransky, D., "Nucleic acid-based methods for the detection of cancer", Science, 278(5340):1054-9 (1997).

Smith et al., "Prostate-specific antigen messenger RNA is expressed in non-prostate cells: implications for detection of micrometastases". Cancer Res. 55:2640-4 (1995).

Soini E, Lovgren T. "Time-resolved fluorescence of lanthanide probes and applications in biotechnology". CRC Crit Rev Anal Chem. 18:105-54 (1987).

Srikantan et al., "PCGEM1, a prostate-specific gene, is overexpressed in prostate cancer". Proc Natl Acad Sci USA Oct. 24, 2000;97(22):12216-21.

Strickler, H.D., and International SV40 Working Group, "A Multicenter Evaluation of Assays for Detection of SV40 DNA and Results in Masked Mesothelioma Specimens," Cancer Epiderniol. Biomarkers Prev. 10:523-532 (May 2001).

Sun Y, Lin J, Katz AE, Fisher PB. Human prostatic carcinoma oncogene PTI-1 is expressed in human tumor cell lines and prostate carcinoma patient blood samples. Cancer Res 1997;57:18-23.

Sutcliffe, J.G. et al., "Antibodies That React with Predetermined Sites on Proteins," Science 219:660-666 (1983).

Syfpeithi at http://134.2.96.221/scripts/MHCServer,d11/home.htm (Mar. 13, 2001).

Tamimi, Y., et al., "DiagnoGene PCA3 reliable NASBA based reagents for detecting PCA3 niRNA, a recently described prostate marker," Proc. Am. Assoc. Cancer Res. 39:234 Poster Abstract (Mar. 1998).

Taneja, S.S., et al., "Chapter 23: Gene Therapy: Principles and Potential," in Cancer Surveys: Preventing Prostate Cancer: Screening versus Chemoprevention, Oliver, R.T.D., et al., eds., Cold Spring Harbor Laboratory Press, pp. 247-266 (1995).

Tinzl et al., "DD3/\PCA3 RNA analysis in urine—a new perspective for detecting prostate cancer." European Urology. 46(2):182-186 (2004).

Tockman, M.S., et al., "Considerations in Bringing a Cancer Biomarker to Clinical Application," Cancer Res. 52:2711s-2718s (1992).

Torres and Marks, "PCS3: A genetic marker of prostate cancer", PCRI Insights. New developments in prostate cancer treatment. 9(3):4-9 (2006).

Tricoli et al., "Detection of Prostate Caner and Predicting Progression: Current and Future Diagnostic Markers," Clin. Cancer Res. 10: 3943-3953, (2004).

Tyagi, S., and Kramer, F.R., "Molecular Beacons: Probes that Fluoresce upon Hybridi7ation," Nat. Biotechnol. 14:303-308 (1996).

Ukimura et al., "Role of PSA and its indices in determining the need for repeat prostate biopsies". Urology 1997;50:66-72.

Vallejo et al., "In vitro synthesis of novel genes: mutagenesis and recombination by PCR", PCR Methods Appl. 4:123-130 (1994).

Vandesompele et al., "Accurate normalization of real-time quantitative RT-PCR data by geometric averaging of multiple internal control genes". Genome Biol 3: RESEARCH0034 (2002).

Verhaegh, G.W., et al., "Characterization of the Prostate-Cancer-Specific DD3 Gene Promoter," Eur. Urol. 38:490, Abstract 10, S. Karger (Oct. 2000).

Verhaegh, G.W., et al., "Isolation and Characterization of the Promoter of the Human Prostate Cancer-specific DD3 Gene," J. Biol. Chem. 275:37496-37503 (Dec. 2000).

Verkaik, N.S. et al., "Clinical usefulness of RT-PCR detection of hematogenous prostate cancer spread," Urol. Res. 25:373-384 (1997).

Verma, I.M., and Somia, N., "Gene therapy—promises, problems and prospects", Nature 389:239-242 (1997).

Voet, D., and Voet, J.G., eds., "Chapter 28: Nucleic Acid Structures and Manipulation," in Biochemistry, 1st Ed., John Wiley & Sons, Inc., San Francisco, CA (1990).

Walker, G.T., et al., "Isothermal in vitro amplification of DNA by a restriction enzyme/DNA polymerase system," Proc, Natl. Acad. Sci. US.A. 89:392-396 (1992).

Walker, G.T., et al., "Strand displacement amplification—an isothermal, in vitro DNA amplification technique," Nucleic Acids Res. 20:1691-1696 (1992).

Watala et al., "Multivariate relationships between international normalized ratio and vitamin K-dependent coagulation-derived parameters in normal healthy donors and oral anticoagulant therapy patients", Thrombosis Journal, 30;1(1):7 (2003).

Wei, C., et al., Tissue-specific expression of the human prostate-specific antigen gene in transgenic mice: Implications for tolerance and immunotherapy, Proc. Natl. Acad. Sci. USA 94:6369-6374 (1997).

Weiss, R., "Hot Prospect for New Gene Amplifier," Science 254:1292-1293 (1991).

Xu et al., "Expression profile of an androgen regulated prostate specific homeobox gene NKX3.1 in primary prostate cancer". J Urol. 163:972-9 (2000).

Yelin et al., "Widespread occurrence of antisense transcription in the human 1, genome," Nat. Biotechnol. 21 :379-386 (Apr. 2003).

Ylikoski et al., "Dual-label detection of amplified products in quantitative RT-PCR assay using lanthanide-labeled probes". Biotechniques. 30:832-6, 838, 840 (2001).

Ylikoski et al., "Quantitative reverse transcription-PCR assay with an internal standard for the detection of prostate-specific antigen mRNA". Clin Chem. 45:1397-407 (1999).

* cited by examiner

SEQUENCE LISTING

<160> NUMBER OF SEQ ID NOS: 13

<210> SEQ ID NO 1
<211> LENGTH: 47
<212> TYPE: DNA
<213> ORGANISM: Homo sapiens

<400> SEQUENCE: 1
aattctaata cgactcacta tagggaggat gaaacaggct gtgccga    47

<210> SEQ ID NO 2
<211> LENGTH: 20
<212> TYPE: DNA
<213> ORGANISM: Homo sapiens

<400> SEQUENCE: 2
agcattccca accctggcag    20

<210> SEQ ID NO 3
<211> LENGTH: 45
<212> TYPE: DNA
<213> ORGANISM: Homo sapiens

<400> SEQUENCE: 3
aattctaata cgactcacta tagggcctgc ccatccttta aggaa    45

<210> SEQ ID NO 4
<211> LENGTH: 20
<212> TYPE: DNA
<213> ORGANISM: Homo sapiens

<400> SEQUENCE: 4
caggaagcac aaaaggaagc    20

<210> SEQ ID NO 5
<211> LENGTH: 24
<212> TYPE: DNA
<213> ORGANISM: Homo sapiens

<400> SEQUENCE: 5
cccagtctgc ggcggtgttc tggg                                          24

<210> SEQ ID NO 6
<211> LENGTH: 28
<212> TYPE: DNA
<213> ORGANISM: Homo sapiens

<400> SEQUENCE: 6
cgcttgtgag ggaaggacat tagaagcg                                      28

<210> SEQ ID NO 7
<211> LENGTH: 506
<212> TYPE: DNA
<213> ORGANISM: Homo sapiens

<400> SEQUENCE: 7
caggaagcac aaaaggaagc acagaggtaa gtgctttata aagcactcaa tttctactca    60 gaaattttg atggccttaa gttcctctac tcgtttctat ccttcctact cactgtcctc   120
ccggaatcca ctaccgattt tctatttctt gcctcgtatt gtctgactgg ctcacttgga   180
tttatcctca cggagtctgg attttctacc cgggctcacc tccgtccctc catatttgtc   240
ctccactttc acagatccct gggagaaatg cccggccgcc atcttgggtc atcgatgagc   300
ctcgccctgt gcctggtccc gcttgtgagg gaaggacatt agaaaatgaa ttgatgtgtt   360
ccttaaagga tgggcaggaa aacagatcct gttgtggata tttatttgaa cgggattaca   420
gatttgaaat gaagtcacca aagtgagcat taccaatgag aggaaaacag acgagaaaat   480
cttgatggct tcacaagaca tgcaac                                       506

<210> SEQ ID NO 8
<211> LENGTH: 278
<212> TYPE: DNA
<213> ORGANISM: Homo sapiens

<400> SEQUENCE: 8
caggaagcac aaaaggaagc acagagatcc ctgggagaaa tgcccggccg ccatcttggg    60
tcatcgatga gcctcgccct gtgcctggtc ccgcttgtga gggaaggaca ttagaaaatg   120
aattgatgtg ttccttaaag gatgggcagg aaaacagatc ctgttgtgga tatttatttg   180
aacgggatta cagatttgaa atgaagtcac caaagtgagc attaccaatg agaggaaaac   240
agacgagaaa atcttgatgg cttcacaaga catgcaac                          278

<210> SEQ ID NO 9
<211> LENGTH: 2036
<212> TYPE: DNA
<213> ORGANISM: Homo sapiens
<220> FEATURE:
<221> NAME/KEY: misc_feature
<222> LOCATION: (1472)..(1472)
<223> OTHER INFORMATION: n is a or c or g or t
<220> FEATURE:
<221> NAME/KEY: misc_feature
<222> LOCATION: (1517)..(1517)
<223> OTHER INFORMATION: n is a or c or g or t
<220> FEATURE:
<221> NAME/KEY: misc_feature
<222> LOCATION: (1563)..(1563)
<223> OTHER INFORMATION: n is a or c or g or t

<400> SEQUENCE: 9

```
agaagctggc atcagaaaaa cagaggggag atttgtgtgg ctgcagccga gggagaccag      60
gaagatctgc atggtgggaa ggacctgatg atacagagga attacaacac atatacttag     120
tgtttcaatg aacaccaaga taaataagtg aagagctagt ccgctgtgag tctcctcagt     180
gacacagggc tggatcacca tcgacggcac tttctgagta ctcagtgcag caaagaaaga     240
ctacagacat ctcaatggca ggggtgagaa ataagaaagg ctgctgactt taccatctga     300
ggccacacat ctgctgaaat ggagataatt aacatcacta gaaacagcaa gatgacaata     360
taatgtctaa gtagtgacat gttttttgcac atttccagcc cctttaaata tccacacaca    420
caggaagcac aaaaggaagc acagagatcc ctgggagaaa tgcccggccg ccatcttggg     480
tcatcgatga gcctcgccct gtgcctggtc ccgcttgtga gggaaggaca ttagaaaatg     540
aattgatgtg ttccttaaag gatgggcagg aaaacagatc ctgttgtgga tatttatttg     600
aacgggatta cagatttgaa atgaagtcac aaagtgagca ttaccaatga gaggaaaaca     660
gacgagaaaa tcttgatggc ttcacaagac atgcaacaaa caaatggaa tactgtgatg      720 acatgaggca gccaagctgg ggaggagata accacggggc agagggtcag gattctggcc     780
ctgctgccta aactgtgcgt tcataaccaa atcatttcat atttctaacc ctcaaaacaa     840
agctgttgta atatctgatc tctacggttc cttctgggcc caacattctc catatatcca     900
gccacactca ttttaatat ttagttccca gatctgtact gtgacctttc tacactgtag      960
aataacatta ctcattttgt tcaaagaccc ttcgtgttgc tgcctaatat gtagctgact    1020 gttttttccta aggagtgttc tggcccaggg gatctgtgaa caggctggga agcatctcaa   1080
gatctttcca gggttatact tactagcaca cagcatgatc attacggagt gaattatcta   1140
atcaacatca tcctcagtgt ctttgcccat actgaaattc atttcccact tttgtgccca   1200
ttctcaagac ctcaaaatgt cattccatta atatcacagg attaactttt tttttttaacc  1260 tggaagaatt caatgttaca tgcagctatg ggaattaat tacatatttt gttttccagt    1320
gcaaagatga ctaagtcctt tatccctccc ctttgtttga tttttttcc agtataaagt    1380 taaaatgctt agccttgtac tgaggctgta tacagcacag cctctcccca tccctccagc   1440
cttatctgtc atcaccatca acccctccca tnysacctaa acaaaatcta acttgtaatt   1500
ccttgaacat gtcaggncat acattrttcc ttctgcctga gaagctcttc cttgtctctt   1560
aantctagaa tgatgtaaag ttttgaataa gttgactatc ttacttcatg caaagaaggg   1620
acacatatga gattcatcat ccatgagaca gcaaatacta aaagtgtaat ttgattataa   1680
gagtttagat aaatatatga aatgcaagak ccacagaggg aatgtttatg gggcacgttt   1740
gtaagcctgg gatgtgaagm aaaggcaggg aacctcatag tatcttatat aatatacttc   1800
atttctctat ctctatcaca atatccaaca agcttttcac agaattcatg cagtgcaaat   1860 cccccaaaggt aacctttatc catttcatgg tgagtgcgct ttagaatttt ggcaaatcat  1920
actggtcact tatctcaact ttgagatgtg tttgtccttg tagttaattg aaagaaatag   1980
ggcactcttg tgagccactt tagggttcac tcctggcaat aaagaattta caaaga        2036
```

<210> SEQ ID NO 10
<211> LENGTH: 3582
<212> TYPE: DNA
<213> ORGANISM: Homo sapiens

<400> SEQUENCE: 10

| | | | | | |
|---|---|---|---|---|---|
| acagaagaaa | tagcaagtgc | cgagaagctg | gcatcagaaa | aacagagggg | agatttgtgt | 60 |
| ggctgcagcc | gagggagacc | aggaagatct | gcatggtggg | aaggacctga | tgatacagag | 120 |
| gaattacaac | acatatactt | agtgtttcaa | tgaacaccaa | gataaataag | tgaagagcta | 180 |
| gtccgctgtg | agtctcctca | gtgacacagg | gctggatcac | catcgacggc | actttctgag | 240 |
| tactcagtgc | agcaaagaaa | gactacagac | atctcaatgg | caggggtgag | aaataagaaa | 300 |
| ggctgctgac | tttaccatct | gaggccacac | atctgctgaa | atggagataa | ttaacatcac | 360 |
| tagaaacagc | aagatgacaa | tataatgtct | aagtagtgac | atgttttgc | acatttccag | 420 |
| cccctttaaa | tatccacaca | cacaggaagc | acaaaggaa | gcacagagat | ccctgggaga | 480 |
| aatgcccggc | cgccatcttg | ggtcatcgat | gagcctcgcc | ctgtgcctgg | tcccgcttgt | 540 |
| gagggaagga | cattagaaaa | tgaattgatg | tgttccttaa | aggatgggca | ggaaaacaga | 600 |
| tcctgttgtg | gatatttatt | tgaacgggat | tacagatttg | aaatgaagtc | acaaagtgag | 660 |
| cattaccaat | gagaggaaaa | cagacgagaa | atcttgatg | gcttcacaag | acatgcaaca | 720 |
| aacaaaatgg | aatactgtga | tgacatgagg | cagccaagct | ggggaggaga | taaccacggg | 780 |
| gcagagggtc | aggattctgg | ccctgctgcc | taaactgtgc | gttcataacc | aaatcatttc | 840 |
| atatttctaa | ccctcaaaac | aaagctgttg | taatatctga | tctctacggt | tccttctggg | 900 |
| cccaacattc | tccatatatc | cagccacact | cattttaat | atttagttcc | cagatctgta | 960 |
| ctgtgacctt | tctacactgt | agaataacat | tactcatttt | gttcaaagac | ccttcgtgtt | 1020 |
| gctgcctaat | atgtagctga | ctgtttttcc | taaggagtgt | tctggcccag | gggatctgtg | 1080 |
| aacaggctgg | gaagcatctc | aagatctttc | cagggttata | cttactagca | cacagcatga | 1140 |
| tcattacgga | gtgaattatc | taatcaacat | catcctcagt | gtctttgccc | atactgaaat | 1200 |
| tcatttccca | cttttgtgcc | cattctcaag | acctcaaaat | gtcattccat | taatatcaca | 1260 |
| ggattaactt | tttttttaa | cctggaagaa | ttcaatgtta | catgcagcta | tgggaattta | 1320 |
| attacatatt | ttgttttcca | gtgcaaagat | gactaagtcc | tttatccctc | cccttgttt | 1380 |
| gattttttt | ccagtataaa | gttaaaatgc | ttagccttgt | actgaggctg | tatacagcac | 1440 |
| agcctctccc | catccctcca | gccttatctg | tcatcaccat | caaccctcc | cataccacct | 1500 |
| aaacaaaatc | taacttgtaa | ttccttgaac | atgtcaggac | atacattatt | ccttctgcct | 1560 |
| gagaagctct | tccttgtctc | ttaaatctag | aatgatgtaa | agttttgaat | aagttgacta | 1620 |
| tcttacttca | tgcaaagaag | ggacacatat | gagattcatc | atcacatgag | acagcaaata | 1680 |
| ctaaaagtgt | aatttgatta | taagagttta | gataaatata | tgaaatgcaa | gagccacaga | 1740 |
| gggaatgttt | atggggcacg | tttgtaagcc | tgggatgtga | agcaaaggca | gggaacctca | 1800 |
| tagtatctta | tataatatac | ttcatttctc | tatctctatc | acaatatcca | acaagctttt | 1860 |
| cacagaattc | atgcagtgca | aatccccaaa | ggtaaccttt | atccatttca | tggtgagtgc | 1920 |
| gctttagaat | tttggcaaat | catactggtc | acttatctca | actttgagat | gtgtttgtcc | 1980 |
| ttgtagttaa | ttgaaagaaa | tagggcactc | ttgtgagcca | ctttagggtt | cactcctggc | 2040 |
| aataaagaat | ttacaaagag | ctactcagga | ccagttgtta | agagctctgt | gtgtgtgtgt | 2100 |
| gtgtgtgtgt | gagtgtacat | gccaaagtgt | gcctctctct | cttgacccat | tatttcagac | 2160 |

-continued

| | | | | |
|---|---|---|---|---|
| ttaaaacaag | catgttttca | aatggcacta | tgagctgcca | atgatgtatc accaccatat | 2220 |
| ctcattattc | tccagtaaat | gtgataataa | tgtcatctgt | taacataaaa aaagtttgac | 2280 |
| ttcacaaaag | cagctggaaa | tggacaacca | caatatgcat | aaatctaact cctaccatca | 2340 |
| gctacacact | gcttgacata | tattgttaga | agcacctcgc | atttgtgggt tctcttaagc | 2400 |
| aaaatacttg | cattaggtct | cagctggggc | tgtgcatcag | gcggtttgag aaatattcaa | 2460 |
| ttctcagcag | aagccagaat | tgaattccc | tcatctttta | ggaatcattt accaggtttg | 2520 |
| gagaggattc | agacagctca | ggtgctttca | ctaatgtctc | tgaacttctg tccctctttg | 2580 |
| tgttcatgga | tagtccaata | aataatgtta | tctttgaact | gatgctcata ggagagaata | 2640 |
| taagaactct | gagtgatatc | aacattaggg | attcaaagaa | atattagatt taagctcaca | 2700 |
| ctggtcaaaa | ggaaccaaga | tacaaagaac | tctgagctgt | catcgtcccc atctctgtga | 2760 |
| gccacaacca | acagcaggac | ccaacgcatg | tctgagatcc | ttaaatcaag gaaaccagtg | 2820 |
| tcatgagttg | aattctccta | ttatggatgc | tagcttctgg | ccatctctgg ctctcctctt | 2880 |
| gacacatatt | agcttctagc | ctttgcttcc | acgactttta | tcttttctcc aacacatcgc | 2940 |
| ttaccaatcc | tctctctgct | ctgttgcttt | ggacttcccc | acaagaattt caacgactct | 3000 |
| caagtctttt | cttccatccc | caccactaac | ctgaattgcc | tagacccta tttttattaa | 3060 |
| tttccaatag | atgctgccta | tgggctaata | ttgctttaga | tgaacattag atatttaaag | 3120 |
| tctaagaggt | tcaaaatcca | actcattatc | ttctctttct | ttcacctccc ctgctcctct | 3180 |
| ccctatatta | ctgattgact | gaacaggatg | gtccccaaga | tgccagtcaa atgagaaacc | 3240 |
| cagtggctcc | ttgtggatca | tgcatgcaag | actgctgaag | ccagaggatg actgattacg | 3300 |
| cctcatgggt | ggaggggacc | actcctgggc | cttcgtgatt | gtcaggagca agacctgaga | 3360 |
| tgctccctgc | cttcagtgtc | ctctgcatct | cccctttcta | atgaagatcc atagaatttg | 3420 |
| ctacatttga | gaattccaat | taggaactca | catgttttat | ctgccctatc aattttttaa | 3480 |
| acttgctgaa | aattaagttt | tttcaaaatc | tgtccttgta | aattacttttt tcttacagtg | 3540 |
| tcttggcata | ctatatcaac | tttgattctt | tgttacaact | tt | 3582 |

<210> SEQ ID NO 11
<211> LENGTH: 7130
<212> TYPE: DNA
<213> ORGANISM: Homo sapiens

<400> SEQUENCE: 11

| | | | | |
|---|---|---|---|---|
| gaattccaca | ttgtttgctg | cacgttggat | tttgaaatgc | tagggaactt tgggagactc | 60 |
| atatttctgg | gctagaggat | ctgtggacca | caagatcttt | ttatgatgac agtagcaatg | 120 |
| tatctgtgga | gctggattct | gggttgggag | tgcaaggaaa | agaatgtact aaatgccaag | 180 |
| acatctattt | caggagcatg | aggaataaaa | gttctagttt | ctggtctcag agtggtgcag | 240 |
| ggatcaggga | gtctcacaat | ctcctgagtg | ctggtgtctt | agggcacact gggtcttgga | 300 |
| gtgcaaagga | tctaggcacg | tgaggctttg | tatgaagaat | cggggatcgt acccacccc | 360 |
| tgtttctgtt | tcatcctggg | catgtctcct | ctgcctttgt | ccctagatg aagtctccat | 420 |
| gagctacaag | ggcctggtgc | atccaggtg | atctagtaat | tgcagaacag caagtgctag | 480 |
| ctctccctcc | ccttccacag | ctctgggtgt | gggagggggt | tgtccagcct ccagcagcat | 540 |
| ggggagggcc | ttggtcagcc | tctgggtgcc | agcagggcag | gggcggagtc ctggggaatg | 600 |
| aaggttttat | agggctcctg | ggggaggctc | cccagcccca | agcttaccac ctgcacccgg | 660 |
| agagctgtgt | caccatgtgg | gtcccggttg | tcttcctcac | cctgtccgtg acgtggattg | 720 |

```
gtgagagggg ccatggttgg ggggatgcag gagagggagc cagccctgac tgtcaagctg    780
aggctctttc cccccaacc cagcacccca gcccagacag ggagctgggc tcttttctgt     840
ctctcccagc cccacttcaa gcccataccc ccagcccctc catattgcaa cagtcctcac    900
tcccacacca ggtccccgct ccctcccact taccccagaa cttctcccc attgcccagc     960 cagctccctg ctcccagctg ctttactaaa ggggaagttc ctgggcatct ccgtgtttct   1020
ctttgtgggg ctcaaaacct ccaaggacct ctctcaatgc cattggttcc ttggaccgta   1080
tcactggtcc atctcctgag cccctcaatc ctatcacagt ctactgactt ttcccattca   1140
gctgtgagtg tccaaccta tcccagagac cttgatgctt ggcctcccaa tcttgccta     1200 ggatacccag atgccaacca gacacctcct tcttcctagc caggctatct ggcctgagac   1260
aacaaatggg tccctcagtc tggcaatggg actctgagaa ctcctcattc cctgactctt   1320
agccccagac tcttcattca gtggcccaca ttttccttag gaaaaacatg agcatcccca   1380
gccacaactg ccagctctct gattcccaa atctgcatcc ttttcaaaac ctaaaaacaa    1440
aaagaaaaac aaataaaaca aaaccaactc agaccagaac tgttttctca acctgggact   1500
tcctaaactt tccaaaacct tcctcttcca gcaactgaac ctggccataa ggcacttatc   1560
cctggttcct agcaccccctt atcccctcag aatccacaac ttgtaccaag tttcccttct   1620
cccagtccaa gaccccaaat caccacaaag gacccaatcc ccagactcaa gatatggtct   1680
gggcgctgtc ttgtgtctcc taccctgatc cctgggttca actctgctcc cagagcatga   1740
agcctctcca ccagcaccag ccaccaacct gcaaacctag ggaagattga cagaattccc   1800
agcctttccc agctcccccct gcccatgtcc caggactccc agccttggtt ctctgccccc   1860
gtgtcttttc aaacccacat cctaaatcca tctcctatcc gagtcccca gttcccctg    1920 tcaaccctga ttccctgat ctagcacccc ctctgcaggc gctgcgcccc tcatcctgtc    1980
tcggattgtg ggaggctggg agtgcgagaa gcattcccaa ccctggcagg tgcttgtggc   2040
ctctcgtggc agggcagtct gcggcggtgt tctggtgcac ccccagtggg tcctcacagc   2100
tgcccactgc atcaggaagt gagtagggc ctggggtctg gggagcaggt gtctgtgtcc    2160
cagaggaata acagctgggc attttcccca ggataacctc taaggccagc cttgggactg   2220
ggggagagag ggaaagttct ggttcaggtc acatggggag gcagggttgg ggctggacca   2280
ccctccccat ggctgcctgg gtctccatct gtgtccctct atgtctcttt gtgtcgcttt   2340
cattatgtct cttggtaact ggcttcggtt gtgtctctcc gtgtgactat tttgttctct   2400
ctctccctct cttctctgtc ttcagtctcc atatctcccc ctctctctgt ccttctctgg   2460
tccctctcta gccagtgtgt ctcaccctgt atctctctgc caggctctgt ctctcggtct   2520
ctgtctcacc tgtgccttct ccctactgaa cacacgcacg ggatgggcct gggggaccc    2580 tgagaaaagg aagggctttg gctgggcgcg gtggctcaca cctgtaatcc cagcactttg   2640
ggaggccaag gcaggtagat cacctgaggt caggagttcg agaccagcct ggccaactgg   2700
tgaaacccca tctctactaa aaatacaaaa aattagccag gcgtggtggc gcatgcctgt   2760
agtcccagct actcaggagg ctgagggagg agaattgctt gaacctggga ggttgaggtt   2820
gcagtgagcc gagaccgtgc cactgcactc cagcctgggt gacagagtga gactccgcct   2880
caaaaaaaaa aaaaaaaaa aaaaaaaaa agaaagaaa agaaagaaa aggaatcttt       2940 tatccctgat gtgtgtgggt atgagggtat gagagggccc ctctcactcc attccttctc   3000
caggacatcc ctccactctt gggagacaca gagaagggct ggttccagct ggagctggga   3060
ggggcaattg agggaggagg aaggagaagg gggaaggaaa acagggtatg ggggaaagga   3120
```

```
ccctggggag cgaagtggag gatacaacct tgggcctgca ggccaggcta cctacccact   3180
tggaaaccca cgccaaagcc gcatctacag ctgagccact ctgaggcctc ccctccccgg   3240
cggtccccac tcagctccaa agtctctctc ccttttctct cccacacttt atcatccccc   3300
ggattcctct ctacttggtt ctcattcttc ctttgacttc ctgcttccct ttctcattca   3360
tctgtttctc actttctgcc tggttttgtt cttctctctc tctttctctg gcccatgtct   3420
gtttctctat gtttctgtct tttcttctc atcctgtgta ttttcggctc accttgtttg   3480
tcactgttct ccctctgcc ctttcattct ctctgtcctt ttaccctctt cctttttccc   3540
ttggtttctc tcagtttctg tatctgccct tcaccctctc acactgctgt ttcccaactc   3600
gttgtctgta tttttggcct gaactgtgtc ttccccaacc ctgtgttttt ctcactgttt   3660
cttttttctct tttggagcct cctccttgct cctctgtccc ttctctcttt ccttatcatc   3720
ctcgctcctc attcctgcgt ctgcttcctc cccagcaaaa gcgtgatctt gctgggtcgg   3780
cacagcctgt ttcatcctga agacacaggc caggtatttc aggtcagcca cagcttccca   3840
cacccgctct acgatatgag cctcctgaag aatcgattcc tcaggccagg tgatgactcc   3900
agccacgacc tcatgctgct ccgcctgtca gagcctgccg agctcacgga tgctgtgaag   3960
gtcatggacc tgcccaccca ggagccagca ctggggacca cctgctacgc ctcaggctgg   4020
ggcagcattg aaccagagga gtgtacgcct gggccagatg gtgcagccgg gagcccagat   4080
gcctgggtct gagggaggag gggacaggac tcctgggtct gagggaggag ggccaaggaa   4140
ccaggtgggg tccagcccac aacagtgttt ttgcctggcc cgtagtcttg accccaaaga   4200
aacttcagtg tgtggacctc catgttattt ccaatgacgt gtgtgcgcaa gttcaccctc   4260
agaaggtgac caagttcatg ctgtgtgctg gacgctggac aggggcaaa agcacctgct   4320
cggtgagtca tccctactcc caagatcttg aggggaaagg tgagtgggga ccttaattct   4380
gggctggggt ctagaagcca acaaggcgtc tgcctcccct gctcccagc tgtagccatg   4440
ccacctcccc gtgtctcatc tcattccctc cttccctctt ctttgactcc ctcaaggcaa   4500
taggttattc ttacagcaca actcatctgt tcctgcgttc agcacacggt tactaggcac   4560
ctgctatgca cccagcactg ccctagagcc tgggacatag cagtgaacag acagagagca   4620
gcccctccct tctgtagccc ccaagccagt gaggggcaca ggcaggaaca gggaccacaa   4680
cacagaaaag ctggagggtg tcaggaggtg atcaggctct cggggaggga aaggggtgg   4740
ggagtgtgac tgggaggaga catcctgcag aaggtgggag tgagcaaaca cctgccgcag   4800
gggaggggag ggccctgcgg cacctggggg agcagaggga acagcatctg gccaggcctg   4860
ggaggagggg cctagagggc gtcaggagca gagaggaggt tgcctggctg gagtgaagga   4920
tcggggcagg gtgcgagagg gaagaaagga cccctcctgc agggcctcac ctgggccaca   4980
ggaggacact gcttttcctc tgaggagtca ggaactgtgg atggtgctgg acagaagcag   5040
gacagggcct ggctcaggtg tccagaggct gccgctggcc tccctatggg atcagactgc   5100
agggagggag ggcagcaggg atgtggaggg agtgatgatg gggctgacct ggggtggct   5160
ccaggcattg tccccacctg ggccttacc cagcctccct cacaggctcc tggccctcag   5220
tctctcccct ccactccatt ctccacctac ccacagtggg tcattctgat caccgaactg   5280
accatgccag ccctgccgat ggtcctccat ggctccctag tgccctggag aggaggtgtc   5340
tagtcagaga gtagtcctgg aaggtggcct ctgtgaggag ccacggggac agcatcctgc   5400
agatggtcct ggcccttgtc ccaccgacct gtctacaagg actgtcctcg tggaccctcc   5460
cctctgcaca ggagctggac cctgaagtcc cttccctacc ggccaggact ggagccccta   5520
```

| | |
|---|---|
| cccctctgtt ggaatccctg cccaccttct tctggaagtc ggctctggag acatttctct | 5580 |
| cttcttccaa agctgggaac tgctatctgt tatctgcctg tccaggtctg aaagatagga | 5640 |
| ttgcccaggc agaaactggg actgacctat ctcactctct ccctgctttt acccttaggg | 5700 |
| tgattctggg ggcccacttg tctgtaatgg tgtgcttcaa ggtatcacgt catggggcag | 5760 |
| tgaaccatgt gccctgcccg aaaggccttc cctgtacacc aaggtggtgc attaccggaa | 5820 |
| gtggatcaag gacaccatcg tggccaaccc ctgagcaccc ctatcaactc cctattgtag | 5880 |
| taaacttgga accttggaaa tgaccaggcc aagactcaag cctccccagt tctactgacc | 5940 |
| tttgtcctta ggtgtgaggt ccaggggttgc taggaaaaga aatcagcaga cacaggtgta | 6000 |
| gaccagagtg tttcttaaat ggtgtaattt tgtcctctct gtgtcctggg gaatactggc | 6060 |
| catgcctgga gacatatcac tcaatttctc tgaggacaca gataggatgg ggtgtctgtg | 6120 |
| ttatttgtgg gatacagaga tgaaagaggg gtgggatcca cactgagaga gtggagagtg | 6180 |
| acatgtgctg gacactgtcc atgaagcact gagcagaagc tggaggcaca acgcaccaga | 6240 |
| cactcacagc aaggatggag ctgaaaacat aacccactct gtcctggagg cactgggaag | 6300 |
| cctagagaag gctgtgagcc aaggagggag ggtcttcctt tggcatggga tggggatgaa | 6360 |
| gtaaggagag ggactggacc ccctggaagc tgattcacta tggggggagg tgtattgaag | 6420 |
| tcctccagac aaccctcaga tttgatgatt tcctagtaga actcacagaa ataaagagct | 6480 |
| cttatactgt ggtttattct ggtttgttac attgacagga gacacactga aatcagcaaa | 6540 |
| ggaaacaggc atctaagtgg ggatgtgaag aaaacaggga aaatctttca gttgttttct | 6600 |
| cccagtgggg tgttgtggac agcacttaaa tcacacagaa gtgatgtgtg accttgtgta | 6660 |
| tgaagtattt ccaactaagg aagctcacct gagccttagt gtccagagtt cttattgggg | 6720 |
| gtctgtagga taggcatggg gtactggaat agctgacctt aacttctcag acctgaggtt | 6780 |
| cccaagagtt caagcagata cagcatggcc tagagcctca gatgtacaaa acaggcatt | 6840 |
| catcatgaat cgcactgtta gcatgaatca tctggcacgg cccaaggccc caggtatacc | 6900 |
| aaggcacttg ggccgaatgt tccaagggat taaatgtcat ctcccaggag ttattcaagg | 6960 |
| gtgagccctg tacttggaac gttcaggctt tgagcagtgc agggctgctg agtcaacctt | 7020 |
| ttactgtaca gggggtgag ggaaagggag aagatgagga aaccgcctag ggatctggtt | 7080 |
| ctgtcttgtg gccgagtgga ccatgggggct atcccaagaa ggaggaattc | 7130 |

```
<210> SEQ ID NO 12
<211> LENGTH: 20
<212> TYPE: DNA
<213> ORGANISM: Homo sapiens

<400> SEQUENCE: 12
```

| | |
|---|---|
| agcattccca accctggcag | 20 |

```
<210> SEQ ID NO 13
<211> LENGTH: 3923
<212> TYPE: DNA
<213> ORGANISM: Homo sapiens

<400> SEQUENCE: 13
```

| | |
|---|---|
| acagaagaaa tagcaagtgc cgagaagctg gcatcagaaa aacagagggg agatttgtgt | 60 |
| ggctgcagcc gagggagacc aggaagatct gcatggtggg aaggacctga tgatacagag | 120 |
| gaattacaac acatatactt agtgtttcaa tgaacaccaa gataaataag tgaagagcta | 180 |
| gtccgctgtg agtctcctca gtgacacagg gctggatcac catcgacggc actttctgag | 240 |

```
tactcagtgc agcaaagaaa gactacagac atctcaatgg caggggtgag aaataagaaa      300
ggctgctgac tttaccatct gaggccacac atctgctgaa atggagataa ttaacatcac      360
tagaaacagc aagatgacaa tataatgtct aagtagtgac atgtttttgc acatttccag      420
cccctttaaa tatccacaca cacaggaagc acaaaaggaa gcacagagat ccctgggaga      480
aatgcccggc cgccatcttg ggtcatcgat gagcctcgcc ctgtgcctgg tcccgcttgt      540
gagggaagga cattagaaaa tgaattgatg tgttccttaa aggatgggca ggaaaacaga      600
tcctgttgtg gatatttatt tgaacgggat tacagatttg aaatgaagtc acaaagtgag      660
cattaccaat gagaggaaaa cagacgagaa aatcttgatg gcttcacaag acatgcaaca      720
aacaaaatgg aatactgtga tgacatgagg cagccaagct ggggaggaga taaccacggg      780
gcagagggtc aggattctgg ccctgctgcc taaactgtgc gttcataacc aaatcatttc      840
atatttctaa ccctcaaaac aaagctgttg taatatctga tctctacggt tccttctggg      900
cccaacattc tccatatatc cagccacact cattttttaat atttagttcc cagatctgta      960
ctgtgacctt tctacactgt agaataacat tactcatttt gttcaaagac ccttcgtgtt     1020
gctgcctaat atgtagctga ctgttttttcc taaggagtgt tctggcccag gggatctgtg     1080
aacaggctgg gaagcatctc aagatctttc cagggttata cttactagca cacagcatga     1140
tcattacgga gtgaattatc taatcaacat catcctcagt gtctttgccc atactgaaat     1200
tcatttccca cttttgtgcc cattctcaag acctcaaaat gtcattccat taatatcaca     1260
ggattaactt ttttttttaa cctggaagaa ttcaatgtta catgcagcta tgggaattta     1320
attacatatt ttgttttcca gtgcaaagat gactaagtcc tttatccctc ccctttgttt     1380
gatttttttt ccagtataaa gttaaaatgc ttagccttgt actgaggctg tatacagcac     1440
agcctctccc catccctcca gccttatctg tcatcaccat caaccccctcc cataccacct     1500 aaacaaaatc taacttgtaa ttccttgaac atgtcaggac atacattatt ccttctgcct     1560
gagaagctct tccttgtctc ttaaatctag aatgatgtaa agttttgaat aagttgacta     1620
tcttacttca tgcaaagaag ggacacatat gagattcatc atcacatgag acagcaaata     1680
ctaaaagtgt aatttgatta taagagttta gataaatata tgaaatgcaa gagccacaga     1740
gggaatgttt atggggcacg tttgtaagcc tgggatgtga agcaaaggca gggaacctca     1800
tagtatctta tataatatac ttcatttctc tatctctatc acaatatcca acaagctttt     1860
cacagaattc atgcagtgca aatccccaaa ggtaaccttt atccatttca tggtgagtgc     1920
gctttagaat tttggcaaat catactggtc acttatctca actttgagat gtgtttgtcc     1980
ttgtagttaa ttgaaagaaa tagggcactc ttgtgagcca ctttagggtt cactcctggc     2040
aataaagaat ttacaaagag ctactcagga ccagttgtta agagctctgt gtgtgtgtgt     2100
gtgtgtgtgt gagtgtacat gccaaagtgt gcctctctct cttgacccat tatttcagac     2160
ttaaaacaag catgttttca aatggcacta tgagctgcca atgatgtatc accaccatat     2220
ctcattattc tccagtaaat gtgataataa tgtcatctgt taacataaaa aaagtttgac     2280
ttcacaaaag cagctggaaa tggacaacca caatatgcat aaatctaact cctaccatca     2340
gctacacact gcttgacata tattgttaga agcacctcgc atttgtgggt tctcttaagc     2400
aaaatacttg cattaggtct cagctggggc tgtgcatcag gcggtttgag aaatattcaa     2460
ttctcagcag aagccagaat ttgaattccc tcatctttta ggaatcattt accaggtttg     2520
gagaggattc agacagctca ggtgctttca ctaatgtctc tgaacttctg tccctctttg     2580
tgttcatgga tagtccaata aataatgtta tctttgaact gatgctcata ggagagaata     2640
```

-continued

```
taagaactct gagtgatatc aacattaggg attcaaagaa atattagatt taagctcaca    2700
ctggtcaaaa ggaaccaaga tacaaagaac tctgagctgt catcgtcccc atctctgtga    2760
gccacaacca acagcaggac ccaacgcatg tctgagatcc ttaaatcaag gaaaccagtg    2820
tcatgagttg aattctccta ttatggatgc tagcttctgg ccatctctgg ctctcctctt    2880
gacacatatt agcttctagc ctttgcttcc acgacttta tcttttctcc aacacatcgc     2940
ttaccaatcc tctctctgct ctgttgcttt ggacttcccc acaagaattt caacgactct    3000
caagtctttt cttccatccc caccactaac ctgaatgcct agacccttat ttttattaat    3060
ttccaataga tgctgcctat gggctatatt gctttagatg aacattagat atttaaagct    3120
caagaggttc aaaatccaac tcattatctt ctctttcttt cacctccctg ctcctctccc    3180
tatattactg attgcactga acagcatggt ccccaatgta gccatgcaaa tgagaaaccc    3240
agtggctcct tgtggtacat gcatgcaaga ctgctgaagc cagaaggatg actgattacg    3300
cctcatgggt ggaggggacc actcctgggc cttcgtgatt gtcaggagca agacctgaga    3360
tgctccctgc cttcagtgtc ctctgcatct cccctttcta atgaagatcc atagaatttg    3420
ctacatttga gaattccaat taggaactca catgttttat ctgccctatc aattttttaa    3480
acttgctgaa aattaagttt tttcaaaatc tgtccttgta aattactttt tcttacagtg    3540
tcttggcata ctatatcaac tttgattctt tgttacaact tttcttactc ttttatcacc    3600
aaagtggctt ttattctctt tattattatt attttctttt actactatat tacgttgtta    3660
ttattttgtt ctctatagta tcaatttatt tgatttagtt tcaatttatt tttattgctg    3720
acttttaaaa taagtgattc gggggggtggg agaacagggg agggagagca ttaggacaaa    3780
tacctaatgc atgtgggact taaaacctag atgatgggtt gataggtgca gcaaaccact    3840
atggcacacg tatacctgtg taacaaacct acacattctg cacatgtatc ccagaacgta    3900
aagtaaaatt taaaaaaaag tga                                            3923
```

METHOD TO DETECT PROSTATE CANCER IN A SAMPLE

CROSS REFERENCE TO RELATED APPLICATIONS

This application is a divisional of U.S. patent application Ser. No. 15/093,214, filed Apr. 7, 2016, which is a divisional of U.S. patent application Ser. No. 14/011,988 filed Aug. 28, 2013, now abandoned, which is a divisional of U.S. patent application Ser. No. 13/470,451 filed May 14, 2012, now U.S. Pat. No. 8,546,551, which is divisional of U.S. patent application Ser. No. 12/500,749 filed Jul. 10, 2009, now U.S. Pat. No. 8,192,931, which is a continuation application of U.S. patent application Ser. No. 10/773,440, filed on Feb. 9, 2004, now abandoned, which claims priority, under 35 U.S.C. § 119(e), of U.S. provisional application Ser. No. 60/445,436, filed on Feb. 7, 2003, each of which is incorporated herein in their entirety by reference for all purposes.

SEQUENCE LISTING

This application contains a Sequence Listing in computer readable form entitled 2018-07-17 01159-0006-05U5 Revised Seq List.txt, created Jul. 17, 2018, having a size of 25 Kb. The computer readable form is incorporated herein by reference.

FIELD OF THE INVENTION

The present invention relates to prostate cancer. More specifically, the present invention relates to a method to detect prostate cancer in a patient sample by detecting an RNA encoded by the prostate cancer antigen PCA3 gene.

BACKGROUND OF THE INVENTION

Over the last decade, cancer of the prostate has become the most commonly diagnosed malignancy among men and the second leading cause of male cancer deaths in the western population, following lung cancer.

Early detection and treatment of prostate cancer before it has spread from the prostate gland, reduces the mortality of the disease. This is particularly true for younger men who are at greater risk of dying from this pernicious but slowly growing malignancy. This realization has prompted increasing efforts for early diagnosis and treatment. Indeed, the American Cancer Society and the American Urological Association recommend that male population at large undergo annual screening for prostate cancer beginning at age 50. The recommended age for screening is lowered to 40 for men giving a family history of prostate cancer or other risk factors.

With this increasing focus on prostate cancer screening, more men than ever before are being routinely tested for prostate cancer. Not surprisingly, this practice has increased early detection of onset of the disease, as reflected by an apparent increase in the incidence of prostate cancer and decrease in the apparent average age of diagnosis. The clinical hope is that earlier detection of prostate cancer before it metastasizes will reduce the overall mortality rate. Healthcare payers look for early screening and detection to translate into a reduction in the healthcare burden, as early treatment can be less radical, more successful and therefore provided at a lower cost per treated patient. The key to accomplishing this goal remains providing better differential diagnostic tools.

Screening for prostate cancer now involves both palpation of the prostate by digital rectal examination (DRE) and assay of plasma levels of prostate specific antigen (PSA/hK3/hKLK3). PSA is a serine protease produced by the prostatic epithelium that is normally secreted in the seminal fluid to liquefy it. Disruption of the anatomic integrity of the prostate gland can compromise the cellular barriers that normally restrict PSA to within the duct system of the prostate, allowing it to disperse into blood or urine. A number of conditions can result in leakage of PSA into the blood. They include inflammation of the prostate, urinary retention, prostatic infection, benign prostatic hyperplasia (BPH), and prostate cancer. Physical manipulation of the prostate can also increase serum PSA levels, but a mild stimulus, such as digital rectal examination (DRE), does not normally increase serum PSA. It is therefore not surprising that screening of serum PSA as an indicator of prostate cancer is not absolutely predictive.

Despite the fact that measure of blood PSA levels can be the result from a variety of different causes, it is nonetheless the basis for primary screening for prostate cancer. Measurement of total PSA (tPSA) as a diagnostic assay to predict prostate cancer has been in use since 1991. Levels of 4 ng/ml or greater in blood serum are considered abnormal and predictive of prostate cancer. However, the sensitivity of such elevated tPSA levels is only 79%; thus leaving 21% of patients with prostate cancer undetected. The specificity for all tPSA values of 4 ng/ml or greater is very poor. In addition, estimates of specificity for tPSA levels>4.0 ng/ml are reported to be in the range of 20% to 59%, averaging around 33%. The vast majority of false positives are ultimately shown to be benign prostatic hyperplasia (BPH). The specificity is lowest for modestly elevated tPSA, in the low so-called gray zone of 4 to 10 ng/ml. This low level of specificity results in additional more invasive and costly diagnostic procedures, such as transrectal ultrasounds and prostate biopsies. Such tests when unnecessary are also very traumatic for the patient. The psychological impact of being diagnosed as positive until proven as a false positive should not be understated either.

Because of the shortcomings of tPSA, research has been focused on attempting to develop PSA derivatives to increase the sensitivity and specificity of this general diagnostic approach.

One modification is free PSA (fPSA), which was FDA approved in 1998. PSA in serum can be found either in an unbound form or complexed with circulating protease inhibitors, most commonly with alpha-1-antitrypsin (ACT). Clinicians have shown that the proportion of PSA bound to ACT was significantly higher in men with prostate cancer than in unaffected men or those with BPH. As a guideline, if 25% or less of total PSA is free, this is an indicator of possible prostate cancer. The fPSA assay was approved for use in men with tPSA's for 4 to 10 ng/ml. Thus, the fPSA assay was positioned to improve the specificity over that of tPSA alone. However, the predictivity of the fPSA test is not as good in people with really low or really high tPSA levels. Very low tPSA, regardless of measured fPSA, is predictive of not having cancer, while the converse is true with very high tPSA levels. The diagnostic usefulness of fPSA is relatively limited as it can be associated with either BPH or prostate cancer. The use of fPSA in combination with tPSA has been shown to reduce the number of unnecessary biopsies by about 20%.

Clearly, prostate biopsy is the gold standard for confirming prostate cancer. However, even a biopsy is not always 100% certain. The standard is the sextant biopsy where tissue sample collection is guided by transrectal ultrasound. Often six samples are not enough to detect the cancer and either a second biopsy procedure or more than six samples are required.

Despite the improvements in prostate cancer screening over the last ten years, there remains a large unmet need in diagnostic sensitivity and specificity, even when these tools are used in combination. Coupling this need with the large incidence of prostate cancer and the importance for early, accurate detection, the potential usefulness for a true differential diagnostic tool is very significant.

A new prostate cancer marker, PCA3, was discovered a few years ago by differential display analysis intended to highlight genes associated with prostate cancer development. PCA3 is located on chromosome 9 and composed of four exons. It encodes at least four different transcripts which are generated by alternative splicing and polyadenylation. By RT-PCR analysis, PCA3 expression was found to be limited to the prostate and absent in all other tissues tested, including testis, ovary, breast and bladder. Northern blot analysis showed that PCA3 is highly expressed in the vast majority of prostate cancers examined (47 out of 50) whereas no or very low expression is detected in BPH or normal prostate cells from the same patients [Cancer Res 1999 Dec. 1; 59(23):5975-9]. Moreover, a recent study comparing the clinical performance of RNA telomerase RT and RNA PCA3 detection in the case of prostate cancer showed that the PCA3 gene can be considered as a better marker (Cancer Res 2002 May 1; 62(9):2695-8).

The PCA3 gene is composed of 4 exons (e1-e4) and 3 introns (i1-i3). While PCA3 appears to be recognized as the best prostate-cancer marker ever identified, this specificity has been contested in the literature. For example, Gandini et al., 2003, claim that the prostate-specific expression of PCA3 is restricted to that of exon 4 of the PCA3 gene. However, the applicants have shown in a recent patent application that this is not the case (Patent application CA 2,432,365).

In view of the fact that advanced prostate cancer remains a life threatening disease reaching a very significant proportion of the male population, there remains a need to provide the most specific, selective, and rapid prostate cancer detection methods and kits.

The present invention seeks to meet these and other needs.

The present description refers to a number of documents, the content of which is herein incorporated by reference in their entirety.

SUMMARY OF THE INVENTION

The present invention relates to diagnostic methods and kits to detect prostate cancer, which are more specific and selective than the methods and kits of the prior art.

The present invention relates to a method to detect prostate cancer in a patient and especially from a urine sample thereof by detecting the RNA encoded by the PCA3 gene.

The invention further relates to a method of diagnosing the presence or predisposition to develop prostate cancer in a patient. Also disclosed is a method for monitoring the progression of prostate cancer in a patient.

In one particular embodiment, the present invention relates to a method to detect prostate cancer in urine samples by detecting the presence of RNA encoded by the PCA3 gene. In one embodiment, RNA encoded by the PCA3 gene is detected using an amplification method, which simultaneously amplifies a second prostate-specific nucleic acid sequence also contained in the sample.

In one further particular embodiment of the present invention, the amplified second prostate specific marker is selected from the group consisting of PSA, human kallikrein 2 (hK2/KLK2), prostate specific membrane antigen (PSMA), transglutaminase 4, acid phosphatase or PCGEM1 RNA.

In another embodiment of the present invention, the RNA is detected using amplification method. In a further embodiment, the RNA amplification method is coupled to real-time detection of the amplified products using fluorescence specific probes. In yet a further embodiment, the amplification method is PCR. In an additional embodiment the PCR is real-time PCR or a related method enabling detection in real-time of the amplified products.

In a related embodiment RNA encoded by the PCA3 gene is detected in a nucleic acid extract by an in vitro RNA amplification method named Nucleic Acid Based Amplification (NASBA). Of course other RNA amplification methods are known and the instant methods and kits are therefore not limited to NASBA. Non-limiting examples of such RNA amplification methods include transcriptase mediated amplification (TMA), strand displacement amplification (SDA) and ligase chain reaction (LCR).

In a further embodiment, the amplified products are detected in a homogenous phase using a fluorescent probe. In one embodiment, the Beacon approach is used. In another embodiment, the product is detected on solid phase using fluorescent or colorimetric method. It should thus be understood that numerous fluorescent, colorimetric or enzymatic methods can be used in accordance with the present invention to detect and/or quantify RNAs. Other types of labelled probes and primers or other types of detection methods may also be used in the present invention (e.g., hybridization assays such as Northern blots, dot blots or slot blots and radiolabelled probes and primers).

In one embodiment, the RNA encoded by the PCA3 gene is obtained from a cell contained in a voided urine sample from the patient.

In another embodiment, the urine sample is obtained after an attentive digital rectal examination (DRE). Of course, it should be understood that the present methods and kits could also be used on a urine sample obtained without DRE, or on other types of samples such as sperm or mixed urine and sperm (e.g., first urine sample following ejaculation), provided that the amplification method and/or detection method is sensitive enough to detect the targeted markers (PCA3 and second marker). Experiments showed that the methods and kits of the present invention can also be performed with these types of samples. Other samples that can be used include blood or serum.

In one embodiment, the cells collected from the urine sample are harvested and a total nucleic acid extraction is carried out. In one particular embodiment, total nucleic acid extraction is carried out using a solid phase band method on silica beads as described by BOOM et al., (1990, J. Clin. Microbiol. 28: 495-503). In another embodiment, the nucleic acids are purified using another target capture method (see below). Of course, it should be understood that numerous nucleic acid extraction and purification methods exist and thus, that other methods could be used in accordance with the present invention. Non-limiting examples include a phenol/chloroform extraction method and target capture purification method (see below). Other such methods are described in herein referenced textbooks. It should also be recognized that numerous means to stabilize or protect the prostate cells contained in the urine sample or other sample, as well as to stabilize or protect the RNA present in these cells are well known in the art.

In another embodiment, the methods of the present invention are carried out using a crude, unpurified, or semi-purified sample.

In one particular embodiment, the present invention also relates to a prostate cancer diagnostic kit for detecting the presence of PCA3 nucleic acid in a sample. Such kit generally comprises a first container means having disposed therein at least one oligonucleotide probe and/or primer that hybridizes to a PCA3 nucleic acid (e.g., PCA3 RNA) and a second container means containing at least one other oligonucleotide primer and/or probe that hybridizes to the above-mentioned second prostate-specific sequence. In another embodiment, a third container means contains a probe which specifically hybridizes to the PCA3 amplification product. In a preferred embodiment, the kit further includes other containers comprising additional components such as an additional oligonucleotide or primer and/or one or more of the following: buffers, reagents to be used in the assay (e.g., wash reagents, polymerases, internal controls (IC) or else) and reagents capable of detecting the presence of bound nucleic acid probe(s)/primer(s). Of course numerous embodiments of the kits of the present invention are possible. For example, the different container means can be divided in amplifying reagents and detection reagents. In one such an embodiment, a first container means contains amplification or hybridization reagents specific for the target nucleic acids of the present invention (e.g., PCA 3, second prostate specific and internal control nucleic acids) and the second container means contains detection reagents. Alternatively, the detection reagents and amplification reagents can be contained in the same container mean.

The present invention in addition relates to a prostate cancer diagnostic kit for detecting the presence of PCA3 nucleic acid in a sample. Such kit generally comprises a first container means having disposed therein at least one oligonucleotide probe and/or primer that hybridizes to a PCA3 mRNA and a second container means containing at least one other oligonucleotide primer and/or probe that hybridizes to the mRNA of the second prostate-specific sequence. In another embodiment, a third container means contains a probe which specifically hybridizes to the PCA3 amplification product. In a yet another embodiment a fourth container means contains a probe which specifically hybridizes to the second prostate specific mRNA. In a preferred embodiment, the kit further includes other containers comprising additional components such as an additional oligonucleotide or primer (e.g., for internal control) and/or one or more of the following: buffers, reagents to be used in the assay (e.g., wash reagents, polymerases, internal control nucleic acid or cells or else) and reagents capable of detecting the presence of bound nucleic acid probe(s)/primer(s). Of course the separation or assembly of reagents in same or different container means is dictated by the types of extraction, amplification or hybridization methods, and detection methods used as well as other parameters including stability, need for preservation etc.

Multiple methods and kits are encompassed by the present invention. For example, the detection and or amplification of the PCA3 nucleic acid sequence does not need to be identical to that of the second prostate specific polynucleotide or other targeted sequences. Thus for example a method or kit which would be RNA based for PCA3 could be DNA based for the second prostate marker or for other targeted sequences.

It should be understood by a person of ordinary skill that numerous statistical methods can be used in the context of the present invention to determine if the test is positive or negative. The decisional tree used is only one non-limiting example of such a statistical method.

Unless defined otherwise, the scientific and technological terms and nomenclature used herein have the same meaning as commonly understood by a person of ordinary skill to which this invention pertains. Commonly understood definitions of molecular biology terms can be found for example in Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.), Rieger et al., Glossary of genetics: Classical and molecular, $5^{th}$ edition, Springer-Verlag, New-York, 1991; Alberts et al., Molecular Biology of the Cell, $4^{th}$ edition, Garland science, New-York, 2002; and, Lewin, Genes VII, Oxford University Press, New-York, 2000. Generally, the procedures of molecular biology methods and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

In the present description, a number of terms are extensively utilized. In order to provide a clear and consistent understanding of the specification and claims, including the scope to be given such terms, the following definitions are provided.

Definitions

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

The present description refers to a number of routinely used recombinant DNA (rDNA) technology terms. Nevertheless, definitions of selected examples of such rDNA terms are provided for clarity and consistency.

As used herein, "nucleic acid molecule" or "polynucleotides", refers to a polymer of nucleotides. Non-limiting examples thereof include DNA (e.g., genomic DNA, cDNA), RNA molecules (e.g., mRNA) and chimeras thereof. The nucleic acid molecule can be obtained by cloning techniques or synthesized. DNA can be double-stranded or single-stranded (coding strand or non-coding strand [antisense]). Conventional ribonucleic acid (RNA) and deoxyribonucleic acid (DNA) are included in the term "nucleic acid" and polynucleotides as are analogs thereof. A nucleic acid backbone may comprise a variety of linkages known in the art, including one or more of sugar-phosphodiester linkages, peptide-nucleic acid bonds (referred to as "peptide nucleic acids" (PNA); Hydig-Hielsen et al., PCT Int'l Pub. No. WO 95/32305), phosphorothioate linkages, methylphosphonate linkages or combinations thereof. Sugar moieties of the nucleic acid may be ribose or deoxyribose, or similar compounds having known substitutions, e.g., 2' methoxy substitutions (containing a 2'-O-methylribofuranosyl moiety; see PCT No. WO 98/02582) and/or 2' halide substitutions. Nitrogenous bases may be conventional bases (A, G, C, T, U), known analogs thereof (e.g., inosine or others; see The Biochemistry of the Nucleic Acids 5-36, Adams et al., ed., 11th ed., 1992), or known derivatives of purine or pyrimidine bases (see, Cook, PCT Int'l Pub. No. WO 93/13121) or "abasic" residues in which the backbone includes no nitrogenous base for one or more residues (Arnold et al., U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more base analogs). The terminology "PCA3 nucleic acid" or "PCA3 polynucleotides" refers to a native PCA3 nucleic acid sequence. In one embodiment, the PCA3 nucleic acid has the sequence has set forth in SEQ ID NOs 9, 10 and 13. In another embodiment, the PCA3 nucleic acid encodes a PCA3 protein. In a further embodiment, the PCA3 nucleic acid is a non-coding nucleic acid sequence. In yet a further embodiment, the PCA3 sequence which is targeted by the PCA3 sequences encompassed by the present invention, is a natural PCA3 sequence found in a patient sample.

The term "recombinant DNA" as known in the art refers to a DNA molecule resulting from the joining of DNA segments. This is often referred to as genetic engineering. The same is true for "recombinant nucleic acid".

The term "DNA segment" is used herein, to refer to a DNA molecule comprising a linear stretch or sequence of nucleotides. This sequence when read in accordance with the genetic code (e.g., an open reading frame or ORF), can encode a linear stretch or sequence of amino acids which can be referred to as a polypeptide, protein, protein fragment and the like.

The terminology "amplification pair" or "primer pair" refers herein to a pair of oligonucleotides (oligos) of the present invention, which are selected to be used together in amplifying a selected nucleic acid sequence by one of a number of types of amplification processes.

"Amplification" refers to any known in vitro procedure for obtaining multiple copies ("amplicons") of a target nucleic acid sequence or its complement or fragments thereof. In vitro amplification refers to production of an amplified nucleic acid that may contain less than the complete target region sequence or its complement. Known in vitro amplification methods include, e.g., transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as Qβ-replicase (e.g., Kramer et al., U.S. Pat. No. 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, and denaturation (e.g., EP Pat. App. Pub. No. 0 320 308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Another known strand-displacement amplification method does not require endonuclease nicking (Dattagupta et al., U.S. Pat. No. 6,087,133). Transcription-mediated amplification is used in the present invention. Those skilled in the art will understand that the oligonucleotide primer sequences of the present invention may be readily used in any in vitro amplification method based on primer extension by a polymerase. (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, Molecular Cloning—A Laboratory Manual, Third Edition, CSH Laboratories). As commonly known in the art, the oligos are designed to bind to a complementary sequence under selected conditions.

As used herein, the term "physiologically relevant" is meant to describe interactions that can modulate a function which is physiologically relevant. In the present invention, encompassed for example the transcription of a gene in its natural setting. Of course a binding of a protein to PCA3 may also be considered as a physiologically relevant function if this binding occur in a natural setting.

The term "DNA" molecule or sequence (as well as sometimes the term "oligonucleotide") refers to a molecule comprised generally of the deoxyribonucleotides adenine (A), guanine (G), thymine (T) and/or cytosine (C). In "RNA", T is replaced by uracil (U). As used herein, particular DNA or RNA sequences may be described according to the normal convention of giving only the sequence in the 5' to 3' direction.

Agarose Gel Electrophoresis. The most commonly used technique (though not the only one) for fractionating double stranded DNA is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. In order to visualize a small subset of these fragments, a methodology referred to as a hybridization procedure (e.g., Southern hybridization) can be applied.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 2000, supra and Ausubel et al., 1994, supra) and are commonly known in the art. In the case of a hybridization to a nitrocellulose filter (or other such support like nylon), as for example in the well known Southern blotting procedure, a nitrocellulose filter can be incubated overnight at 65° C. with a labeled probe in a solution containing high salt (6×SSC or 5×SSPE), 5×Denhardt's solution, 0.5% SDS, and 100 µg/ml denatured carrier DNA (e.g., salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The salt and SDS concentration of the washing solutions may also be adjusted to accommodate for the desired stringency. The selected temperature and salt concentration is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 2000, supra). Other protocols or commercially available hybridization kits (e.g., ExpressHyb™ from BD Biosciences Clonetech) using different annealing and washing solutions can also be used as well known in the art.

A "probe" is meant to include a nucleic acid oligomer that hybridizes specifically to a target sequence in a nucleic acid or its complement, under conditions that promote hybridization, thereby allowing detection of the target sequence or its amplified nucleic acid. Detection may either be direct (i.e, resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e, a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled.

By "sufficiently complementary" is meant a contiguous nucleic acid base sequence that is capable of hybridizing to another sequence by hydrogen bonding between a series of complementary bases. Complementary base sequences may be complementary at each position in sequence by using standard base pairing (e.g., G:C, A:T or A:U pairing) or may contain one or more residues (including abasic residues) that are not complementary by using standard base pairing, but which allow the entire sequence to specifically hybridize with another base sequence in appropriate hybridization conditions. Contiguous bases of an oligomer are preferably at least about 80% (81, 82, 83, 84, 85, 86, 87, 88, 89, 90, 91, 92, 93, 94, 95, 96, 97, 98, 99, 100%), more preferably at least about 90% complementary to the sequence to which the oligomer specifically hybridizes. Appropriate hybridization conditions are well known to those skilled in the art, can be predicted readily based on sequence composition and conditions, or can be determined empirically by using routine testing (see Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly at §§ 9.50-9.51, 11.12-11.13, 11.45-11.47 and 11.55-11.57).

Nucleic acid sequences may be detected by using hybridization with a complementary sequence (e.g., oligonucleotide probes) (see U.S. Pat. No. 5,503,980 (Cantor), U.S. Pat. No. 5,202,231 (Drmanac et al.), U.S. Pat. No. 5,149,625 (Church et al.), U.S. Pat. No. 5,112,736 (Caldwell et al.), U.S. Pat. No. 5,068,176 (Vijg et al.), and U.S. Pat. No. 5,002,867 (Macevicz)). Hybridization detection methods may use an array of probes (e.g., on a DNA chip) to provide sequence information about the target nucleic acid which selectively hybridizes to an exactly complementary probe sequence in a set of four related probe sequences that differ one nucleotide (see U.S. Pat. Nos. 5,837,832 and 5,861,242 (Chee et al.)).

A detection step may use any of a variety of known methods to detect the presence of nucleic acid by hybridization to a probe oligonucleotide. One specific example of a detection step uses a homogeneous detection method such as described in detail previously in Arnold et al., *Clinical Chemistry* 35:1588-1594 (1989), and U.S. Pat. No. 5,658,737 (Nelson et al.), and U.S. Pat. Nos. 5,118,801 and 5,312,728 (Lizardi et al.).

The types of detection methods in which probes can be used include Southern blots (DNA detection), dot or slot blots (DNA, RNA), and Northern blots (RNA detection). Labeled proteins could also be used to detect a particular nucleic acid sequence to which it binds (e.g., protein detection by far western technology: Guichet et al., 1997, Nature 385(6616): 548-552; and Schwartz et al., 2001, EMBO 20(3): 510-519). Other detection methods include kits containing reagents of the present invention on a dipstick setup and the like. Of course, it might be preferable to use a detection method which is amenable to automation. A non-limiting example thereof includes a chip or other support comprising one or more (e.g., an array) of different probes.

A "label" refers to a molecular moiety or compound that can be detected or can lead to a detectable signal. A label is joined, directly or indirectly, to a nucleic acid probe or the nucleic acid to be detected (e.g., an amplified sequence). Direct labeling can occur through bonds or interactions that link the label to the nucleic acid (e.g., covalent bonds or non-covalent interactions), whereas indirect labeling can occur through use a "linker" or bridging moiety, such as additional oligonucleotide(s), which is either directly or indirectly labeled. Bridging moieties may amplify a detectable signal. Labels can include any detectable moiety (e.g., a radionuclide, ligand such as biotin or avidin, enzyme or enzyme substrate, reactive group, chromophore such as a dye or colored particle, luminescent compound including a bioluminescent, phosphorescent or chemiluminescent compound, and fluorescent compound). Preferably, the label on a labeled probe is detectable in a homogeneous assay system, i.e., in a mixture, the bound label exhibits a detectable change compared to an unbound label.

Other methods of labeling nucleic acids are known whereby a label is attached to a nucleic acid strand as it is fragmented, which is useful for labeling nucleic acids to be detected by hybridization to an array of immobilized DNA probes (e.g., see PCT No. PCT/IB99/02073).

A "homogeneous detectable label" refers to a label whose presence can be detected in a homogeneous fashion based upon whether the labeled probe is hybridized to a target sequence. A homogeneous detectable label can be detected without physically removing hybridized from unhybridized forms of the labeled probe. Homogeneous detectable labels and methods of detecting them have been described in detail elsewhere (e.g., see U.S. Pat. Nos. 5,283,174, 5,656,207 and 5,658,737).

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well known methods. While they are usually in a single-stranded form, they can be in a double-stranded form and even contain a "regulatory region". They can contain natural rare or synthetic nucleotides. They can be designed to enhance a chosen criteria like stability for example.

As used herein, a "primer" defines an oligonucleotide which is capable of annealing to a target sequence, thereby creating a double stranded region which can serve as an initiation point for nucleic acid synthesis under suitable conditions. Primers can be, for example, designed to be specific for certain alleles so as to be used in an allele-specific amplification system. For example, a primer can be designed so as to be complementary to a short PCA3 RNA which is associated with a malignant state of the prostate, whereas a long PCA3 RNA is associated with a non-malignant state (benign) thereof (PCT/CA00/01154 published under No. WO 01/23550). The primer's 5' region may be non-complementary to the target nucleic acid sequence and include additional bases, such as a promoter sequence (which is referred to as a "promoter primer"). Those skilled in the art will appreciate that any oligomer that can function as a primer can be modified to include a 5' promoter sequence, and thus function as a promoter primer. Similarly, any promoter primer can serve as a primer, independent of its functional promoter sequence. Of course the design of a primer from a known nucleic acid sequence is well known in the art. As for the oligos, it can comprise a number of types of different nucleotides.

Transcription-associated amplification. Amplifying a target nucleic acid sequence by using at least two primers can be accomplished using a variety of known nucleic acid amplification methods, but preferably uses a transcription-associated amplification reaction that is substantially isothermal. By using such an in vitro amplification method, many strands of nucleic acid are produced from a single copy of target nucleic acid, thus permitting detection of the target in the sample by specifically binding the amplified sequences to one or more detection probes. Transcription-associated amplification methods have been described in detail elsewhere (e.g., U.S. Pat. Nos. 5,399,491 and 5,554,516). Briefly, transcription-associated amplification uses two types of primers (one being a promoter primer because it contains a promoter sequence for an RNA polymerase), two enzyme activities (a reverse transcriptase (RT) and an RNA polymerase), substrates (deoxyribonucleoside triphosphates, ribonucleoside triphosphates) and appropriate salts and buffers in solution to produce multiple RNA transcripts from a nucleic acid template. Initially, a promoter primer hybridizes specifically to a target sequence (e.g., RNA) and reverse transcriptase creates a first complementary DNA strand (cDNA) by extension from the 3' end of the promoter primer. The cDNA is made available for hybridization with the second primer by any of a variety of methods, such as, by denaturing the target-cDNA duplex or using RNase H activity supplied by the RT that degrades RNA in a DNA:RNA duplex. A second primer binds to the cDNA and a new strand of DNA is synthesized from the end of the second primer using the RT activity to create a double-stranded DNA (dsDNA) having a functional promoter sequence at one end. An RNA polymerase binds to the dsDNA promoter sequence and transcription produces multiple transcripts ("amplicons"). Amplicons are used in subsequent steps or cycles of the transcription-associated amplification process by serving as a new template for replication, thus generating many copies of amplified nucleic acid (i.e., about 100 to 3,000 copies of RNA are synthesized from each template).

NASBA. Nucleic Acid Sequence Based Amplification (NASBA) can be carried out in accordance with known techniques (Malek et al., Methods Mol Biol, 28:253-260). In an embodiment, the NASBA amplification starts with the annealing of an antisense primer P1 (containing the T7 RNA polymerase promoter) to the mRNA target. Reverse transcriptase (RTase) then synthesizes a complementary DNA strand. The double stranded DNA/RNA hybrid is recognized by RNase H that digests the RNA strand, leaving a single-stranded DNA molecule to which the sense primer P2 can bind. P2 serves as an anchor to the RTase that synthesizes a second DNA strand. The resulting double-stranded DNA has a functional T7 RNA polymerase promoter recognized by the respective enzyme. The NASBA reaction can then enter in the phase of cyclic amplification comprising six steps: (1) Synthesis of short antisense single-stranded RNA molecules ($10^1$ to $10^3$ copies per DNA template) by the T7 RNA polymerase; (2) annealing of primer P2 to these RNA molecules; (3) synthesis of a complementary DNA strand by RTase; (4) digestion of the RNA strand in the DNA/RNA hybrid; (5) annealing of primer P1 to the single-stranded DNA; and (6) generation of double stranded DNA molecules by RTase. Because the NASBA reaction is isothermal (41° C.), specific amplification of ssRNA is possible if denaturation of dsDNA is prevented in the sample preparation procedure. It is thus possible to pick up RNA in a dsDNA background without getting false positive results caused by genomic dsDNA.

Polymerase chain reaction (PCR). Polymerase chain reaction can be carried out in accordance with known techniques. See, e.g., U.S. Pat. Nos. 4,683,195; 4,683,202; 4,800,159; and 4,965,188 (the disclosures of all three U.S. Patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review on PCR techniques (see PCR Protocols, A Guide to Methods and Amplifications, Michael et al., Eds, Acad. Press, 1990).

Ligase chain reaction (LCR) can be carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

Target capture. In one embodiment, target capture is included in the method to increase the concentration or purity of the target nucleic acid before in vitro amplification. Preferably, target capture involves a relatively simple method of hybridizing and isolating the target nucleic acid, as described in detail elsewhere (e.g., see U.S. Pat. Nos. 6,110,678, 6,280,952, and 6,534,273). Generally speaking, target capture can be divided in two family, sequence specific and non sequence specific. In the non-specific method, a reagent (e.g., silica beads) is used to capture non specifically nucleic acids. In the sequence specific method an oligonucleotide attached to a solid support is contacted with a mixture containing the target nucleic acid under appropriate hybridization conditions to allow the target nucleic acid to be attached to the solid support to allow purification of the target from other sample components. Target capture may result from direct hybridization between the target nucleic acid and an oligonucleotide attached to the solid support, but preferably results from indirect hybridization with an oligonucleotide that forms a hybridization complex that links the target nucleic acid to the oligonucleotide on the solid support. The solid support is preferably a particle that can be separated from the solution, more preferably a paramagnetic particle that can be retrieved by applying a magnetic field to the vessel. After separation, the target nucleic acid linked to the solid support is washed and amplified when the target sequence is contacted with appropriate primers, substrates and enzymes in an in vitro amplification reaction.

Generally, capture oligomer sequences include a sequence that specifically binds to the target sequence, when the capture method is indeed specific, and a "tail" sequence that links the complex to an immobilized sequence by hybridization. That is, the capture oligomer includes a sequence that binds specifically to its PCA3 or to another prostate specific marker (e.g., PSA, hK2/KLK2, PMSA, transglutaminase 4, acid phosphatase, PCGEM1) target sequence and a covalently attached 3' tail sequence (e.g., a homopolymer complementary to an immobilized homopolymer sequence). The tail sequence which is, for example, 5 to 50 nucleotides long, hybridizes to the immobilized sequence to link the target-containing complex to the solid support and thus purify the hybridized target nucleic acid from other sample components. A capture oligomer may use any backbone linkage, but some embodiments include one or more 2'-methoxy linkages. Of course, other capture methods are well known in the art. The capture method on the cap structure (Edery et al., 1988, gene 74(2): 517-525, U.S. Pat. No. 5,219,989) or the silica based method are two non-limiting examples of capture methods.

An "immobilized probe" or "immobilized nucleic acid" refers to a nucleic acid that joins, directly or indirectly, a capture oligomer to a solid support. An immobilized probe is an oligomer joined to a solid support that facilitates separation of bound target sequence from unbound material in a sample. Any known solid support may be used, such as matrices and particles free in solution, made of any known material (e.g., nitrocellulose, nylon, glass, polyacrylate, mixed polymers, polystyrene, silane polypropylene and metal particles, preferably paramagnetic particles). Preferred supports are monodisperse paramagnetic spheres (i.e., uniform in size ±about 5%), thereby providing consistent results, to which an immobilized probe is stably joined directly (e.g., via a direct covalent linkage, chelation, or ionic interaction), or indirectly (e.g., via one or more linkers), permitting hybridization to another nucleic acid in solution.

The term "allele" defines an alternative form of a gene which occupies a given locus on a chromosome.

Gene. A DNA sequence generally related but not necessarily related to a single polypeptide chain or protein, and as used herein includes the 5' and 3' untranslated regions. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("RNA").

Structural Gene. A DNA sequence that is transcribed into RNA that is then translated into a sequence of amino acids characteristic of a specific polypeptide(s).

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. A mutant polypeptide can be encoded from this mutant nucleic acid molecule.

As used herein, the term "purified" refers to a molecule (e.g., nucleic acid) having been separated from a component of the composition in which it was originally present. Thus, for example, a "purified nucleic acid" has been purified to a level not found in nature. A "substantially pure" molecule is a molecule that is lacking in most other components (e.g., 30, 40, 50, 60, 70, 75, 80, 85, 90, 95, 96, 97, 98, 99, 100% free of contaminants). By opposition, the term "crude" means molecules that have not been separated from the components of the original composition in which it was present. For the sake of brevity, the units (e.g., 66, 67 . . . 81, 82, . . . 91, 92% . . . ) have not been specifically recited but are considered nevertheless within the scope of the present invention.

As used herein the terminology "prostate specific marker" relates to any molecule whose presence in the sample indicates that such sample contains prostate cells (or a marker therefrom). Therefore a "prostate specific sequence" refers to a nucleic acid or protein sequence specifically found in prostate cells and usually not in other tissues which could "contaminate" a particular sample. For certainty, when a urine sample is used, the second prostate specific marker according to the present invention does not have to be solely expressed in the prostate. In fact markers which are solely expressed in one organ or tissue is very rare. However, should the second prostate specific marker be expressed in non-prostate tissue, this non prostate tissue expression will not jeopardized the specificity of this second marker provided that it occurs in cells of tissues or organs which are not normally present in the urine sample. Thus, when urine is the sample, this second prostate-specific marker is not normally expressed in other types of cells (e.g., cells from the urinary tract system) to be found in the urine sample.

Control sample. By the term "control sample" or "normal sample" is meant here a sample that does not contain a specifically chosen cancer. In a particular embodiment, the control sample does not contain prostate cancer or is indicative of the absence of prostate cancer. Control samples can be obtained from patients/individuals not afflicted with prostate cancer. Other types of control samples may also be used. For example, a prostate specific marker can be used as to make sure that the sample contains prostate specific cells (this marker is generally described herein as the second prostate-specific marker). In a related aspect, a control reaction may be designed to control the method itself (e.g., The cell extraction, the capture, the amplification reaction or detection method, number of cells present in the sample, a combination thereof or any step which could be monitored to positively validate that the absence of a signal (e.g., the absence of PCA3 signal) is not the result of a defect in one ore more of the steps).

Cut-off value. The cut-off value for the predisposition or presence of prostate cancer is defined from a population of patients without prostate cancer as the average signal of PCA3 (or other prostate cancer antigen) polynucleotides, polypeptides or fragments thereof plus n standard deviations (or average mean signal thereof). Cut off values indicative of the presence or predisposition to develop prostate cancer may be the same or alternatively, they may be different values.

Variant. The term "variant" refers herein to a protein or nucleic acid molecule which is substantially similar in structure and biological activity to the protein or nucleic acid of the present invention, to maintain at least one of its biological activities. Thus, provided that two molecules possess a common activity and can substitute for each other, they are considered variants as that term is used herein even if the composition, or secondary, tertiary or quaternary structure of one molecule is not identical to that found in the other, or if the amino acid sequence or nucleotide sequence is not identical.

A "biological sample" or "sample of a patient" is meant to include any tissue or material derived from a living or dead human which may contain the PCA3 target nucleic acid and second prostate specific marker. Samples include, for example, any tissue or material that may contain cells specific for the PCA3 target (or second specific marker), such as peripheral blood, plasma or serum, biopsy tissue, gastrointestinal tissue, bone marrow, urine, feces, semen or other body fluids, tissues or materials, but preferably is a urine sample following digital rectal examination (or other means which increase the content of prostate cells in urine). The biological sample may be treated to physically disrupt tissue or cell structure, thus releasing intracellular components into a solution which may further contain enzymes, buffers, salts, detergents, and the like which are used to prepare the sample for analysis.

Other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

Having thus, generally described the invention, reference will be made to the accompanying drawings, showing by way of illustration only an illustrative embodiment thereof and in which.

DESCRIPTION OF ILLUSTRATIVE EMBODIMENTS

Figure 1:
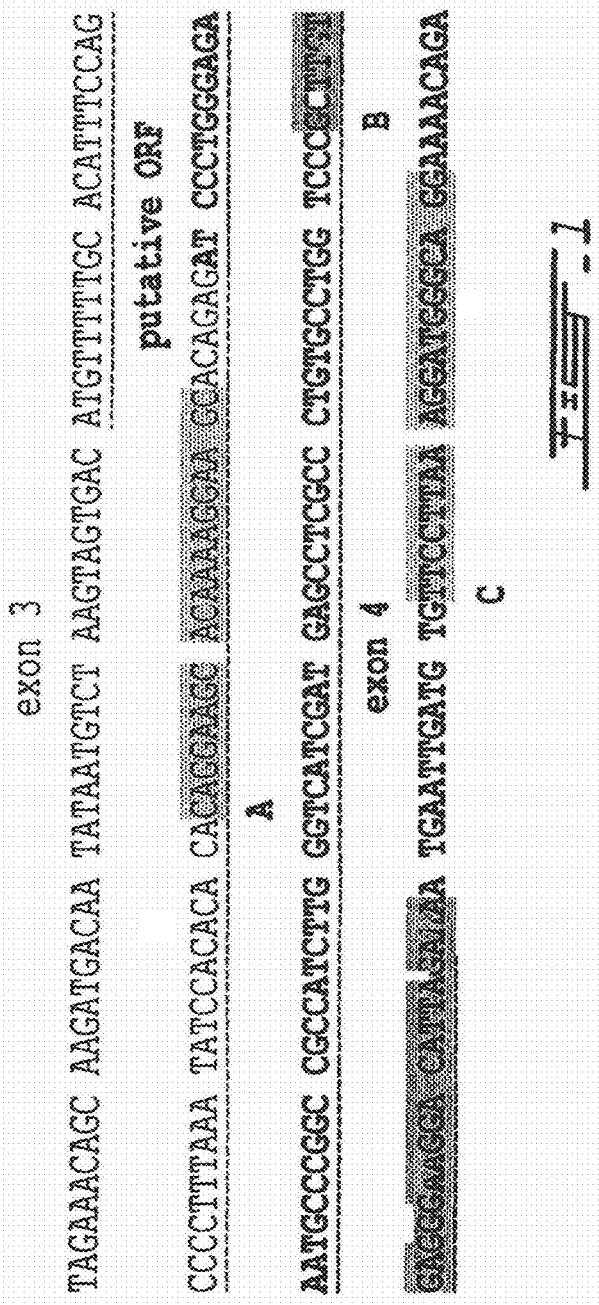
FIG. 1 shows the PCA3 gene structure and location of oligonucleotides and probes for in vitro RNA amplification and amplified product detection. In accordance with one embodiment of the present invention. Panel A. Targeting zone of sense PCA3 primer (SEQ ID NO 4); Panel B. Targeting zone of PCA3 molecular beacon (SEQ ID NO 6); and Panel C. Targeting zone of anti-sense PCA3 primer (SEQ ID NO 3).

For purposes of clarity of disclosure, and not by way of limitation, the detailed description of the invention is divided into the following subsections:
I. A Method to Assess the Presence of Prosate Cancer in a Sample by Detecting PCA3 Nucleic Acid.
II. Synthesis of Nucleic Acid.
III. Probes and Primers.
IV. A Kit for Detecting the Presence of PCA3 Nucleic Acid in a Sample.
I. A Method to Assess the Presence of Prosate Cancer in a Sample by Detecting PCA3 Nucleic Acid The invention encompasses methods for detecting the presence of a PCA3 nucleic acid together with a second prostate specific marker (e.g., PSA, hK2/KLK2, PSMA, transglutaminase 4, acid phophatase, PCGEM1) in a biological sample as well as methods for measuring the level of a PCA3 nucleic acid in the sample. Such methods are useful for the diagnostic of prostate cancers associated with PCA3 overexpression.

The predisposition to develop prostate cancer or the presence of such cancer may be detected based on the presence of an elevated amount of PCA3 nucleic acid in a biological sample (e.g., urine) of a patient. Polynucleotides primers and probes may be used to detect the level of PCA3 RNA present, which is indicative of the predisposition, presence or absence of prostate cancer. In general the elevated amount of PCA3 nucleic acid (e.g., PCA3 mRNA or fragments thereof) in a sample as compared to the amount present in a normal control samples (or a determined cut-off value) indicates that the sample contains prostate cancer or is susceptible to develop prostate cancer. In one embodiment, the detection of a second prostate-specific marker is also performed to serve as a control for the presence of prostate specific cells in the sample as well as to further validate the PCA3 detection results (e.g., a negative result obtained with the detection of PCA3).

Of course, a number of different prostate specific marker can be used as long as they can serve as a control for prostate RNA. Non-limiting examples of such prostate-specific markers include PSA (SEQ ID NO: 11) and other Kallikrein family members. In addition and as described above, markers such as hK2/KLK2, PSMA, transglutaminase 4, acid phosphatase, PCGEM1 can also be used in accordance with the present invention.

One non limiting example of a method to detect PCA3 nucleic acid (e.g., PCA3 mRNA) in a biological sample is by (1) contacting a biological sample with at least one oligonucleotide probe or primer that hybridizes to a PCA3 polynucleotide; and (2) detecting in the biological sample a level of oligonucleotide (i.e. probe(s) or primer(s)) that hybridizes to the PCA3 polynucleotide. The sample is also tested for the presence of second prostate-specific marker (e.g., PSA, hK2/KLK2, PSMA, transglutaminase 4, acid phosphatase, PCGEM1 mRNA or fragments thereof) to control for the presence of prostate cells in the sample (or their number) as well as to further control a negative or positive result obtained with the detection of PCA3. The second prostate specific marker may also be a prostate specific PCA3 RNA that is not associated with prostate cancer but is expressed in prostate cells. The amount of PCA3 polynucleotide detected can be compared with a predetermined cut off value, and therefrom the predisposition, presence or absence of a prostate cancer in the patient is determined.

In a related aspect, the methods of the present invention can be used for monitoring the progression of prostate cancer in a patient. In this particular embodiment, the assays described above are performed over time and the variation in the level of PCA3 nucleic acid and of another prostate specific marker (e.g., PSA mRNA) present in the sample (e.g., urine sample) is evaluated. In general, prostate cancer is considered as progressing when the relative (i.e. relatively to the amount of cells or cell components (e.g., protein or nucleic acids present therein) level of PCA3 nucleic acid detected increases with time. In contrast a cancer is not considered as progressing when the relative level of PCA3 nucleic acid either decreases or remains constant over time.

One skilled in the art can select the nucleic acid primers according to techniques known in the art as described above. Samples to be tested include but should not be limited to RNA samples from human tissue.

In a related aspect, it is possible to verify the efficiency of nucleic acid amplification and/or detection only, by performing external control reaction(s) using highly purified control target nucleic acids added to the amplification and/or detection reaction mixture. Alternatively, the efficiency of nucleic acid recovery from cells and/or organelles, the level of nucleic acid amplification and/or detection inhibition (if present) can be verified and estimated by adding to each test sample control cells or organelles (e.g., a define number of cells from a prostate cancer cell line expressing PCA3 and second marker) by comparison with external control reaction(s). To verify the efficiency of both, sample preparation and amplification and/or detection, such external control reaction(s) may be performed using a reference test sample or a blank sample spiked with cells, organelles and/or viral particles carrying the control nucleic acid sequence(s). For example, a signal from the internal control (IC) sequences present into the cells, viruses and/or organelles added to each test sample that is lower than the signal observed with the external control reaction(s) may be explained by incomplete lysis and/or inhibition of the amplification and/or detection processes for a given test sample. On the other hand, a signal from the IC sequences that is similar to the signal observed with the external control reaction(s), would confirm that the sample preparation including cell lysis is efficient and that there is no significant inhibition of the amplification and/or detection processes for a given test sample. Alternatively, verification of the efficiency of sample preparation only may be performed using external control(s) analyzed by methods other than nucleic acid testing (e.g., analysis using microscopy, mass spectrometry or immunological assays).

Therefore, in one particular embodiment, the methods of the present invention uses purified nucleic acids, prostate cells or viral particles containing nucleic acid sequences serving as targets for an internal control (IC) in nucleic acid test assays to verify the efficiency of cell lysis and of sample preparation as well as the performance of nucleic acid amplification and/or detection. More broadly, the IC serves to verify any chosen step of the process of the present invention.

IC in PCR or related amplification techniques can be highly purified plasmid DNA either supercoiled, or linearized by digestion with a restriction endonuclease and repurified. Supercoiled IC templates are amplified much less efficiently (about 100 fold) and in a less reproducible manner than linearized and repurified IC nucleic acid templates. Consequently, IC controls for amplification and detection of the present invention are preferably performed with linearized and repurified IC nucleic acid templates when such types of IC are used.

The nucleic acids, cells, and/or organelles are incorporated into each test sample at the appropriate concentration to obtain an efficient and reproducible amplification/detection of the IC, based on testing during the assay optimization. The optimal number of control cells added, which is dependent on the assay, is preferentially the minimal number of cells which allows a highly reproducible IC detection signal without having any significant detrimental effect on the amplification and/or detection of the other genetic target(s) of the nucleic acid-based assay. A sample to which is added the purified linearized nucleic acids, cells, viral particles or organelles is generally referred to as a "spiked sample".

Within certain embodiments, the amount of mRNA may be detected via a RT-PCR based assay. In RT-PCR, the polymerase chain reaction (PCR) is applied in conjunction with reverse transcription. In such an assay, at least two oligonucleotide primers may be used to amplify a portion of PCA3 cDNA derived from a biological sample, wherein at least one oligonucleotide is specific for (i.e. hybridizes to) a PCA3 RNA. The amplified cDNA may then be separated and detected using techniques that are well known in the art such as gel electrophoresis and ethidium bromide staining. Amplification may be performed on biological samples taken from a test patient and an individual who is not afflicted with a prostate cancer (control sample), or using other types of control samples. The amplification reaction may be performed on several dilutions of cDNA (or directly on several dilutions of the biological sample) spanning, for example, two orders of magnitude. A value above a predetermined cut off value is indicative of the presence or predisposition to develop prostate cancer. In general, the elevated expression of PCA3 nucleic acid in a biological sample as compared to control samples indicates the presence or the predisposition to develop prostate cancer.

In further embodiments, PCA3 RNA is detected in a nucleic acid extract from a biological sample by an in vitro RNA amplification method named Nucleic Acid Sequence-Based Amplification (NASBA). Other mRNA amplification methods well known in the art may also be used and include transcriptase-mediated amplification (TMA), strand displacement amplification (SDA), the Qβ replicase system and Ligase chain reaction (LCR) (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, Molecular Cloning—A Laboratory Manual, Third Edition, CSH Laboratories).

The amplification and/or detection of prostate cancer specific PCA3 RNA sequences and of the prostate specific marker can be carried out simultaneously (e.g., multiplex real-time amplification assays.)

Alternatively, oligonucleotide probes that specifically hybridize under stringent conditions to a PCA3 nucleic acid may be used in a nucleic acid hybridization assay (e.g., Southern and Northern blots, dot blot, slot blot, in situ hybridization and the like) to determine the presence and/or amount of prostate cancer specific PCA3 polynucleotide in a biological sample.

Alternatively, oligonucleotides and primers could be designed to directly sequence and assess the presence of prostate cancer specific PCA3 sequences in the patient sample following an amplification step. Such sequencing-based diagnostic methods are automatable and are encompassed by the present invention.

II. Synthesis of Nucleic Acid

The nucleic acid (e.g., DNA or RNA) for practicing the present invention may be obtained according to well known methods.

Isolated nucleic acid molecules of the present invention are meant to include those obtained by cloning as well as those chemically synthesized. Similarly, an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185-3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like. Of course the labeling of a nucleic acid sequence can be carried out by other methods known in the art.

III. Probes and Primers

The present invention relates to a nucleic acid for the specific detection, in a sample, of the presence of PCA3 nucleic acid sequences which are associated with prostate cancer, comprising the above-described nucleic acid molecules or at least a fragment thereof which binds under stringent conditions to PCA3 nucleic acid.

In one preferred embodiment, the present invention relates to oligos which specifically target and enable amplification (i.e. primers) of PCA3 RNA sequences associated with prostate cancer.

In another embodiment, PCA3 RNA can be detected using a specific probe in an hybridization assay (e.g., Northern blot, dot blot, slot blot and the like).

Oligonucleotide probes or primers of the present invention may be of any suitable length, depending on the particular assay format and the particular needs and targeted sequences employed. In a preferred embodiment, the oligonucleotide probes or primers are at least 10 nucleotides in length (preferably, 10, 11, 12, 13, 14, 15, 16, 17, 18, 19, 20, 21, 22, 23, 24, 25, 26, 27, 28, 29, 30, 31, 32 . . . ) and they may be adapted to be especially suited for a chosen nucleic acid amplification system. Longer probes and primers are also within the scope of the present invention as well known in the art. Primers having more than 30, more than 40, more than 50 nucleotides and probes having more than 100, more than 200, more than 300, more than 500 more than 800 and more than 1000 nucleotides in length are also covered by the present invention. Of course, longer primers have the disadvantage of being more expensive and thus, primers having between 12 and 30 nucleotides in length are usually designed and used in the art. As well known in the art, probes ranging from 10 to more than 2000 nucleotides in length can be used in the methods of the present invention. As for the % of identity described above, non-specifically described sizes of probes and primers (e.g., 16, 17, 31, 24, 39, 350, 450, 550, 900, 1240 nucleotides, . . . ) are also within the scope of the present invention. In one embodiment, the oligonucleotide probes or primers of the present invention specifically hybridize with a PCA3 RNA (or its complementary sequence). More preferably, the primers and probes will be chosen to detect a PCA3 RNA which is associated with prostate cancer. In one embodiment, the probes and primers used in the present invention do not hybridize with the PCA3 gene (i.e. enable the distinction gene and expressed PCA3). Other primers of the present invention are specific for a second prostate-specific marker such as PSA (SEQ ID NO 11). Of course other variants well known in the art can also be used (U.S. Pat. Nos. 6,479,263 and 5,674,682) as second prostate specific marker. Because of the structural and sequence similarities of the PSA gene with other members of the kallikrein gene family, the appropriate selection of PSA sequences to serve as PSA-specific probes or primers is critical to methods of amplification and/or detection of PSA specific nucleic acids. Examples of suitable primers for PSA, hK2/KLK2, PSMA, amplification and detection (e.g., U.S. Pat. No. 6,551,778) are well known in the art as well as for transglutaminase 4, acid phosphatase and PCGEM1. In one embodiment, the PSA oligonucleotide may also hybridize to other kallikrein family members such as kallikrein 2 (hK2/hKLK2). One example of such oligonucleotide is SEQ ID no 12.

As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1994, in Current Protocols in Molecular Biology, John Wiley & Sons Inc., N.Y.).

To enable hybridization to occur under the assay conditions of the present invention, oligonucleotide primers and probes should comprise an oligonucleotide sequence that has at least 70% (at least 71%, 72%, 73%, 74%), preferably at least 75% (75%, 76%, 77%, 78%, 79%, 80%, 81%, 82%, 83%, 84%, 85%, 86%, 87%, 88%, 89%) and more preferably at least 90% (90%, 91%, 92%, 93%, 94%, 95%, 96%, 97%, 98%, 99%, 100%) identity to a portion of a PCA3 polynucleotide. Probes and primers of the present invention are those that hybridize to PCA3 nucleic acid (e.g., cDNA or mRNA) sequence under stringent hybridization conditions and those that hybridize to PCA3 gene homologs under at least moderately stringent conditions. In certain embodiments probes and primers of the present invention have complete sequence identity to PCA3 gene sequence (e.g., cDNA or mRNA). However, probes and primers differing from the native PCA3 gene sequence that keep the ability to hybridize to native PCA3 gene sequence under stringent conditions may also be used in the present invention. It should be understood that other probes and primers could be easily designed and used in the present invention based on the PCA3 nucleic acid sequence disclosed herein (SEQ ID NOs 9, 10 and 13) by using methods of computer alignment and sequence analysis known in the art (cf. *Molecular Cloning: A Laboratory Manual*, Third Edition, edited by Cold Spring Harbor Laboratory, 2000).

For example, a primer can be designed so as to be complementary to a short PCA3 RNA which is associated with a malignant state of the prostate cancer, whereas a long PCA3 RNA is associated with a non-malignant state (benign) thereof (PCT/CA00/01154 published under No. WO 01/23550). In accordance with the present invention, the use of such a primer with the other necessary reagents would give rise to an amplification product only when a short PCA3 RNA (e.g., SEQ ID NO: 8) associated with prostate cancer is present in the sample. The longer PCA3 (e.g., SEQ ID NO: 7) would not give rise to an amplicon. Of course, the amplification could be designed so as to amplify a short and a long PCA3 mRNA. In such a format, the long PCA3 mRNA could be used as the second prostate specific marker.

In an embodiment as described above, the quantification of the amplification products of short versus long PCA3 could be carried out together with the detection of another prostate specific marker to serve as a molecular diagnostic test for prostate cancer. In another embodiment, primer pairs (or probes) specific for PCA3 could be designed to avoid the detection of the PCA3 gene or of unspliced PCA3 RNA. For example, the primers sequences to be used in the present invention could span two contiguous exons so that it cannot hybridize to an exon/intron junction of the PCA3 gene. The amplification product obtained by the use of such primer would be intron less between two chosen exons (for examples of such primers and probes see table 1 and 2 below). Therefore, unspliced variants and genomic DNA would not be amplified. It will be recognized by the person of ordinary skill that numerous probes can be designed and used in accordance with a number of embodiments of the present invention. Such tests can be adapted using the sequence of PCA3 and that of the second prostate-specific marker. Of course, different primer pairs (and probes) can be designed from any part of the PCA3 sequences (SEQ ID NOs: 7, 8, 9, 10 and 13) as well as from the sequence of PSA (genbank accession number M27274, SEQ ID NO 11) or any other chosen second prostate specific marker (e.g., KLK2 (genbank acc. No. NM005551), PSMA (genbank acc. No. BC025672), transglutaminase 4 (genbank acc. No. BC007003), acid phosphatase (genbank acc. No. BC016344), PCGEM 1 (genbank acc. No. AF223389)).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well-known methods (Sambrook et al., 2000, supra). Non-limiting examples of detectable markers and labels include $^3$H, $^{14}$C, $^{32}$P, and $^{35}$S, ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol I of E. coli in the presence of radioactive dNTP (e.g., uniformly labeled DNA probe using random oligonucleotide primers), using the SP6/T7 system to transcribe a DNA segment in the presence of one or more radioactive NTP, and the like.

In one embodiment, the label used in a homogenous detection assay is a chemiluminescent compound (e.g., U.S. Pat. Nos. 5,656,207, 5,658,737 and 5,639,604), more preferably an acridinium ester ("AE") compound, such as standard AE or derivatives thereof. Methods of attaching labels to nucleic acids and detecting labels are well known (e.g., see Sambrook et al., *Molecular Cloning, A Laboratory Manual*, 2nd ed. (Cold Spring Harbor Laboratory Press, Cold Spring Harbor, N Y, 1989), Chapt. 10; U.S. Pat. Nos. 5,658,737; 5,656,207; 5,547,842; 5,283,174 and 4,581,333; and European Pat. App. No. 0 747 706). Preferred methods of labeling a probe with an AE compound attached via a linker have been previously described detail (e.g., see U.S. Pat. No. 5,639,604, Example 8).

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR, RT PCR . . . ), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, supra). Other non-limiting examples of amplification methods include rolling circle amplification (RCA); signal mediated amplification of RNA technology (SMART); split complex amplification reaction (SCAR); split promoter amplification of RNA (SPAR).

Non-limiting examples of suitable methods to detect the presence of the amplified products include the followings: agarose or polyacrylamide gel, addition of DNA labeling dye in the amplification reaction (such as ethidium bromide, picogreen, SYBER green, etc.) and detection with suitable apparatus (fluorometer in most cases). Other suitable methods include sequencing reaction (either manual or automated); restriction analysis (provided restriction sites were built into the amplified sequences), or any method involving hybridization with a sequence specific probe (Southern or Northern blot, TaqMan™ probes, molecular beacons, and the like). Of course, other amplification methods are encompassed by the present invention. Molecular beacons are exemplified herein as one method for detecting the amplified products according to the present invention (see below).

Of course in some embodiment direct detection (e.g., sequencing) of PCA3 cancer specific sequences as well as that of another prostate specific marker in a sample may be performed using specific probes or primers.

In one embodiment, the present invention has taken advantage of technological advances in methods for detecting and identifying nucleic acids. Therefore, the present invention is suitable for detection by one of these tools called molecular beacons.

Molecular beacons are single-stranded oligonucleotide hybridization probes/primers that form a stem loop structure. The loop contains a probe sequence that is complementary to a target sequence, and the stem is formed by the annealing of complementary arm sequences that are located on either side of the probe/primer sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo comformational change that enables them to fluoresce brightly (see U.S. Pat. Nos. 5,925,517; and 6,037,130). Molecular beacons can be used as amplicon detector probes/primers in diagnostic assays. Because nonhybridized molecular beacons are dark, it is not necessary to isolate the probe-target hybrids to determine for example, the number of amplicons synthesized during an assay. Therefore, molecular beacons simplify the manipulations that are often required when traditional detection and identifications means are used.

By using different colored fluorophores, molecular beacons can also be used in multiplex amplification assays such as assays that target the simultaneous amplification and detection of PCA3 nucleic acid and of the second specific prostate nucleic acid (e.g., PSA, hK2/KLK2, PSMA, transglutaminase 4, acid phosphatase and PCGEM1). The design of molecular beacons probes/primers is well known in the art and softwares dedicated to help their design are commercially available (e.g., Beacon designer from Premier Biosoft International). Molecular beacon probes/primers can be used in a variety of hybridization and amplification assays (e.g., NASBA and PCR).

In accordance with one embodiment of the present invention, the amplified product can either be directly detected using molecular beacons as primers for the amplification assay (e.g., real-time multiplex NASBA or PCR assays) or indirectly using, internal to the primer pair binding sites, a molecular beacon probe of 18 to 25 nucleotides long (e.g., 18, 19, 20, 21, 22, 23, 24, 25) which specifically hybridizes to the amplification product. Molecular beacons probes or primers having a length comprised between 18 and 25 nucleotides are preferred when used according to the present invention (Tyagi et al., 1996, Nature Biotechnol. 14: 303-308). Shorter fragments could result in a less fluorescent signal, whereas longer fragments often do not increase significantly the signal. Of course shorter or longer probes and primers could nevertheless be used.

Examples of nucleic acid primers which can be derived from PCA3 RNA sequences are shown hereinbelow in Table 1:

TABLE 1

NUCLEIC ACID PRIMERS

| | Size (no. of bases) | Nucleotides |
|---|---|---|
| Exon 1 | 98 | 1-98 of SEQ ID NO: 9 |
| Exon 2 | 165 | 99-263 of SEQ ID NO: 9 |
| Exon 3 | 183 | 264-446 of SEQ ID NO: 9 |
| Exon 4a | 539 | 447-985 of SEQ ID NO: 9 |
| Exon 4b | 1052 | 986-2037 of SEQ ID NO: 9 |
| Exon 1 | 120 | 1-120 of SEQ ID NO: 10 |
| Exon 2 | 165 | 121-285 of SEQ ID NO: 10 |
| Exon 3 | 183 | 286-468 of SEQ ID NO: 10 |
| Exon 4a | 539 | 469-1007 of SEQ ID NO: 10 |
| Exon 4b | 1059 | 1008-2066 of SEQ ID NO: 10 |
| Exon 4c | 556 | 2067-2622 of SEQ ID NO: 10 |
| Exon 4d | 960 | 2623-3582 of SEQ ID NO: 10 |
| Exon junction 1 | 20 | 89-108 of SEQ ID NO: 9 |
| Exon junction 1 | 20 | 109-128 of SEQ ID NO: 10 |
| Exon junction 2 | 20 | 252-271 of SEQ ID NO: 9 |
| Exon junction 2 | 20 | 274-293 of SEQ ID NO: 10 |
| Exon junction 3 | 20 | 435-454 of SEQ ID NO: 9 |
| Exon junction 3 | 20 | 457-476 of SEQ ID NO: 10 |
| Exon junction 4 | 20 | 974-993 of SEQ ID NO: 9 |
| Exon junction 4 | 20 | 996-1015 of SEQ ID NO: 10 |
| Exon junction 5 | 20 | 2055-2074 of SEQ ID NO: 10 |
| Exon junction 6 | 20 | 2611-2630 of SEQ ID NO: 10 |

It should be understood that the sequences and sizes of the primers taught in Table 1 are arbitrary and that a multitude of other sequences can be designed and used in accordance with the present invention.

While the present invention can be carried out without the use of a probe which targets PCA3 sequences, such as the exon junctions of PCA3 in accordance with the present invention, such probes can add a further specificity to the methods and kits of the present invention. Examples of specific nucleic acid probes which can be used in the present invention (and designed based on the exonic sequences shown in Table 1) are set forth in Table 2, below:

TABLE 2

NUCLEIC ACID PROBES

| | Size (no. of bases) | Nucleotides |
|---|---|---|
| Probe 1 | 20 | 1-20 of SEQ ID NO: 9 |
| Probe 2 | 30 | 1-30 of SEQ ID NO: 9 |
| Probe 3 | 40 | 1-40 of SEQ ID NO: 9 |
| Probe 4 | 20 | 1-20 of SEQ ID NO: 10 |
| Probe 5 | 30 | 1-30 of SEQ ID NO: 10 |
| Probe 6 | 40 | 1-40 of SEQ ID NO: 10 |
| Probe 7 | 20 | 89-108 of SEQ ID NO: 9 |
| Probe 8 | 30 | 114-143 of SEQ ID NO: 10 |
| Probe 9 | 30 | 257-286 of SEQ ID NO: 9 |
| Probe 10 | 20 | 284-303 of SEQ ID NO: 10 |
| Probe 11 | 20 | 274-293 of SEQ ID NO: 9 |

Of course, as will be understood by the person of ordinary skill, a multitude of additional probes can be designed from the same or other region of SEQ ID NO. 9 as well as from SEQ ID NO. 10 and 13 and other sequences of the present invention, whether they target exon junctions or not. It will be clear that the sizes of the probes taught in Table 2 are arbitrary and that a multitude of other sequences can be designed and used in accordance with the present invention.

It will be readily recognized by the person of ordinary skill, that the nucleic acid sequences of the present invention (e.g., probes and primers) can be incorporated into anyone of numerous established kit formats which are well known in the art.

In one embodiment of the above-described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids (e.g., urine). The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized. Preferably the sample is a urine sample. When the urine sample is used, it should contain at least one prostate cell in order to enable the identification of the prostate specific marker of the present invention. In fact, assuming that the half-life of PCA3 mRNA in an untreated biological sample is not suitable for easily enabling the preservation of the integrity of its sequence, the collected sample, whether urine or otherwise, should, prior to a treatment thereof contain at least one prostate cell. It will be recognized that the number of cells in the sample will have an impact on the validation of the test and on the relative level of measured PCA3 (or second prostate specific marker).

IV. A Kit for Detecting the Presence of PCA3 Nucleic Acid in a Sample

In another embodiment, the present invention relates to a kit for diagnosing prostate cancer in a manner which is both sensitive and specific (i.e., lowering the number of false positives). Such kit generally comprises a first container means having disposed therein at least one oligonucleotide probe or primer that hybridizes to a prostate cancer-specific PCA3 nucleic acid sequence. In one embodiment, the present invention also relates to a kit further comprising in a second container means oligonucleotide probes or primers which are specific to a second prostate specific marker, thereby validating a negative result with PCA3.

In a particular embodiment of the present invention, this kit (K) comprises a primer pair which enables the amplification of PSA, hK2/KLK2, PSMA, transglutaminase 4, acid phosphatase and PCGEM1) Of course the present invention also encompasses the use of a third prostate specific marker.

Oligonucleotides (probes or primers) of the kit may be used, for example, within a NASBA, PCR or hybridization assay. Amplification assays may be adapted for real time detection of multiple amplification products (i.e., multiplex real time amplification assays).

In a related particular embodiment, the kit further includes other containers comprising additional components such as additional oligonucleotide or primer and/or one or more of the following: buffers, reagents to be used in the assay (e.g., wash reagents, polymerases or else) and reagents capable of detecting the presence of bound nucleic acid probe or primers. Examples of detection reagents include, but are not limited to radiolabelled probes, enzymatic labeled probes (horse radish peroxidase, alkaline phosphatase), and affinity labeled probes (biotin, avidin, or steptavidin). In one embodiment, the detection reagents are molecular beacon probes which specifically hybridizes to the amplification products. In another embodiment, the detection reagents are chemiluminescent compounds such as Acridinium Ester (AE).

For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross contaminated and the agents or solutions of each container can be added in a quantitative fashion from one compartment to another. Such containers will include a container which will accept the test sample (e.g., an RNA extract from a biological sample or cells), a container which contains the primers used in the assay, containers which contain enzymes, containers which contain wash reagents, and containers which contain the reagents used to detect the extension products. As mentioned above, the separation or combination of reagents can be adapted by the person of ordinary skill to which this invention pertain, according to the type of kit which is preferred (e.g., a diagnostic kit based on amplification or hybridization methods or both), the types of reagents used and their stability or other intrinsic properties. In one embodiment, one container contains the amplification reagents and a separate container contains the detection reagent. In another embodiment, amplification and detection reagents are contained in the same container.

Kits may also contain oligonucleotides that serve as capture oligomers for purifying the target nucleic acids from a sample. Examples of capture oligomers have sequences of at least 15 nucleotides complementary to a portion of the PCA3 target nucleic acid. Embodiments of capture oligomers may have additional bases attached to a 3' or 5' end the sequence that is complementary to the PCA3 target sequence which may act functionally in a hybridization step for capturing the target nucleic acid. Such additional sequences are preferably a homopolymeric tail sequence, such as a poly-A or poly-T sequence, although other embodiments of tail sequences are included in capture oligomers of the present invention. In one embodiment, CAP binding protein (e.g., eIF4G-4E) or part thereof may be used to capture cap-structure containing mRNAs (Edery et al., 1987, Gene 74(2): 517-525). In another embodiment, a non-specific capture reagent is used (e.g., silica beads).

Kits useful for practicing the methods of the present invention may include those that include any of the amplification oligonucleotides and/or detection probes disclosed herein which are packaged in combination with each other. Kits may also include capture oligomers for purifying the PCA3 target nucleic acid from a sample, which capture oligomers may be packaged in combination with the amplification oligonucleotides and/or detection probes.

In a further embodiment, cells contained in voided urine samples obtained after an attentive digital rectal examination are harvested and lysed in a lysis buffer. Nucleic acids are extracted (e.g., from the lysate by solid phase extraction on silica beads for example). Detection of the presence of RNA encoded by the PCA3 gene in the nucleic acid extract is done by an in vitro specific RNA amplification coupled to real-time detection of amplified products by fluorescent specific probes. In this method, simultaneously to the amplification of the PCA3 prostate cancer specific RNA undergoes the amplification of the second prostate-specific marker (such as the PSA RNA) as a control for the presence in the urine sample of prostate cells.

The screening and diagnostic methods of the invention do not require that the entire PCA3 RNA sequence be detected. Rather, it is only necessary to detect a fragment or length of nucleic acid that is sufficient to detect the presence of the PCA3 nucleic acid from a normal or affected individual, the absence of such nucleic acid, or an altered structure of such nucleic acid (such as an aberrant splicing pattern). For this purpose, any of the probes or primers as described above are used, and many more can be designed as conventionally known in the art based on the sequences described herein and others known in the art.

It is to be understood that although the following discussion is specifically directed to human patients, the teachings are also applicable to any animal that expresses PCA3.

The diagnostic and screening methods of the invention are especially useful for a patient suspected of being at risk for developing a disease associated with an altered expression level of PCA3 based on family history, or a patient in which it is desired to diagnose a PCA3-related disease (ex. prostate cancer). The method of the present invention may also be used to monitor the progression of prostate cancer in patient as described above.

The present invention is illustrated in further details by the following non-limiting example. The examples are provided for illustration only and should not be construed as limiting the scope of the invention.

EXAMPLE 1

Clinical Performance Using One Illustrative Embodiment of the Methods of the Present Invention To estimate the clinical performance of the method, a pilot study was done on 517 patients planned to undergo ultrasound guided needle biopsies coming from five university medical centers located in Montreal and Quebec (Canada) between September 2001 and June 2002. Each sample was processed using the following steps:

Sample Collection

Following an attentive digital rectal examination, the first 20 to 30 ml of voided urine was collected in sterile 80 ml plastic containers (patient urinates directly in the sterile container).

An equal volume of Sample buffer (0.1M phosphate (0.06M $Na_2HPO_4$, 0.04M $NaH_2PO_4$) 0.3M NaCl, pH 7.0,) was immediately added and the solution mixed by inversion.

If not processed immediately, samples were refrigerated between 2-8° C. for up to three days until further processing. In view of the cell recovery step, freezing should be avoided.

Cell Recovery

The sample was mixed by inversion; and the container gently tapped on the counter in order to detach cells from the inner walls thereof. The sample was then transferred into one or two (if necessary) conical polypropylene tubes (40 ml/tube).

The cells were pelleted by centrifugation in a tabletop centrifuge at 1400 g for 15 minutes. Finally, the supernatant was decanted and the cells were immediately lysed.

Cell Lysis

400 µl of Lysis Buffer (4.68M GuSCN, 20 mM EDTA, 1.2% Triton X-100™, 46 mM Tris-HCl, pH 7.2) was added to the urine cell pellet.

The cell pellet was then vigorously vortexed for 20 seconds in order to lyse the cells. It is important to make sure that no particulate matter is left. The lysate was transparent and not too viscous.

The lysate was transferred into a 1.5 ml microtubes and vortexed for 30 seconds.

If desired, the lysed cells can now be stored at ≤−70° C. indefinitely.

Nucleic Acid Extraction

The silica suspension (60 g silica type ±80% particle size 1-5 µm, add MilliQ water at a final volume of 500 ml) was first vigorously vortexed for 30 seconds until an opaque homogeneous suspension was obtained.

200 µl of the suspension was then immediately removed and added to the lysed specimen. All tubes were subsequently vigorously vortexed for 15 seconds to bind nucleic acids to the silica.

On a test tube rack, a series of Microspin™ Columns identifying each filter unit with the appropriate number of patient were prepared.

The content of each microtube containing the lysed cells and the silica were transferred into the membrane filter unit of one Microspin™ Column. To facilitate the transfer of the particulate matter, the microtube was vortexed briefly (approximately 5 seconds) in order to resuspend the content. The same was done before transferring. Tips were changed between samples.

The Microspin™ columns were centrifuged in a non-refrigerated microcentrifuge at 10,000 RPM for 5 minutes at room temperature (18° C.-25° C.). The membrane filter retained silica-bound nucleic acids whereas other cellular components remained in the flow-through.

Meanwhile, a series of 2 ml microtubes corresponding to the number of Microspin™ columns were prepared.

The membrane filter units containing the silica were transferred to new 2 mL microtubes. 500 µl of Wash Buffer (5.3M GuSCN, 52 mM Tris-HCl pH 6.4) was added to each membrane filter unit. The Microspin™ columns were then centrifuged in a non-refrigerated microfuge at 10,000 RPM for 5 minutes at room temperature.

On a test tube rack, a new series of 2 ml microtubes were prepared.

The membrane filter units with the silica were transferred to the new 2 ml microtubes. 600 µl ethanol 70% was added to the membrane filter units. The Microspin™ columns were then centrifuged in a non-refrigerated microfuge at 10,000 RPM for 5 minutes at room temperature.

On a test tube rack, a new series of 2 ml microtubes were prepared.

The membrane filter units with the silica are transferred to a new 2 ml microtube. Discard the microtubes containing the flow-through.

The membrane filter unit containing microtubes were then transferred to a heating block at 65° C.±1° C. installed under a fume hood.

All tubes were opened carefully to ensure evaporation, and incubated for approximately 10 minutes to dry the silica.

200 µl Elution Buffer (Dnase/Rnase-free water) to each membrane filter unit was added.

The membrane filter units were then centrifuged in a microfuge at 10,000 RPM for 5 minutes at room temperature.

The elution steps were repeated once to obtain a second eluate. These steps elute nucleic acids from the silica and concentrate them in the flow-through.

The microfilter units were disposed and the two microtubes containing the nucleic acid elution were kept.

For each eluate, three aliquots of ≅50 µl of nucleic acids were stored at ≤−70° C.

In Vitro RNA Amplification and Detection

The nucleic acid eluate sample to test was first thawed on ice. The reaction mix was then prepared according to the number of reactions to be performed. Each sample was made at least in duplicate.

10 µl of the reaction mix was distributed in identified microtubes [80 mM Tris-HCl pH 8.5, 24 mM $MgCl_2$, 180 mM KCl, 10 mM DTT, 2 mM of each dNTP, 4 mM of rATP, rUTP, CTP, 3 mM rGTP, 1 mM ITP, 30% DMSO, 3% sucrose, 1% D-Mannitol, 1% Dextran T-40, 208 nM PSA primers (N2psaP1B, SEQ. ID NO 1 and N2psaP2B, SEQ. ID NO 2), 417 nM PCA-3 primers (N0pcaP1A, SEQ. ID NO 3 and N0pcaP2B, SEQ. ID NO 4), 84 nM PSA beacon (BpsaRD-4, SEQ. ID NO 5), 166 nM PCA-3 beacon (BpcaFD-4, SEQ. ID NO 6).

5 µl of nucleic acid sample eluate was added in each tube and mixed.

Tubes were placed in a Thermocycler™, heated at 65° C.±1° C. for a period of 5 minutes and then the temperature was kept at 41° C. After 5 minutes at 41° C., tubes were retrieved and centrifuged briefly in order to remove the condensation drops from the lids.

The next steps were better carried out quickly, and the tube temperature was preferably kept at 41° C.

5 µl of the enzyme mix (375 mM sorbitol, 0.105 µg/µl BSA, 0.08 units of RnaseH, 32.0 units of T7 RNA polymerase, 6.4 units of AMV-RT) was then quickly added to each tube and the tubes were gently mixed.

The tubes were put back into the EasyQ™ incubator. When the last tube was in place, the incubator was kept at a temperature of 41° C.±0.5° C. for 5 minutes.

The tubes were then briefly centrifuged. Quickly, all tubes were transferred in a thermostated spectrofluorimeter for in vitro RNA amplification and real time amplified product detection with the following characteristics: (1) the light source was a quartz-halogen lamp, (2) the filter used for ROX (6-carboxy-x-rhodamine N-succinimidyl ester) fluorescence was at 550-620 nm and for FAM (6-carboxyfluorescein N-hydroxysuccinimide ester) was at 485-530 nm, (3) the fluorescence integration time per tube was 20 msec; and (4) ROX and FAM emission was read each 30 sec and the tube block was set at the temperature of 41° C.±1° C.

Results

Fluorescence data generated during the two hours of amplification underwent fitting following the approach of Brown [Computer Methods and Programs in Biomedicine 65 (2001) 191-200].

Based on the PSA ratio (fluo max/fluo min) cut off of 1.3, out of the 517 patients who have been tested, 443 had adequate quantities of prostate cells in the urine.

In this population of patients, 34% (151/443) had prostate cancer confirmed by histology.

TABLE 3

Positive Biopsies versus tPSA Categories

| tPSA | Percentage of Patients | Positive Biopsies |
| --- | --- | --- |
| <4 ng/ml | 21% (n = 94) | 20% (n = 19) |
| 4-10 ng/ml | 55% (n = 243) | 35% (n = 85) |
| >10 ng/ml | 24% (n = 106) | 44% (n = 47) |

Figure 2:
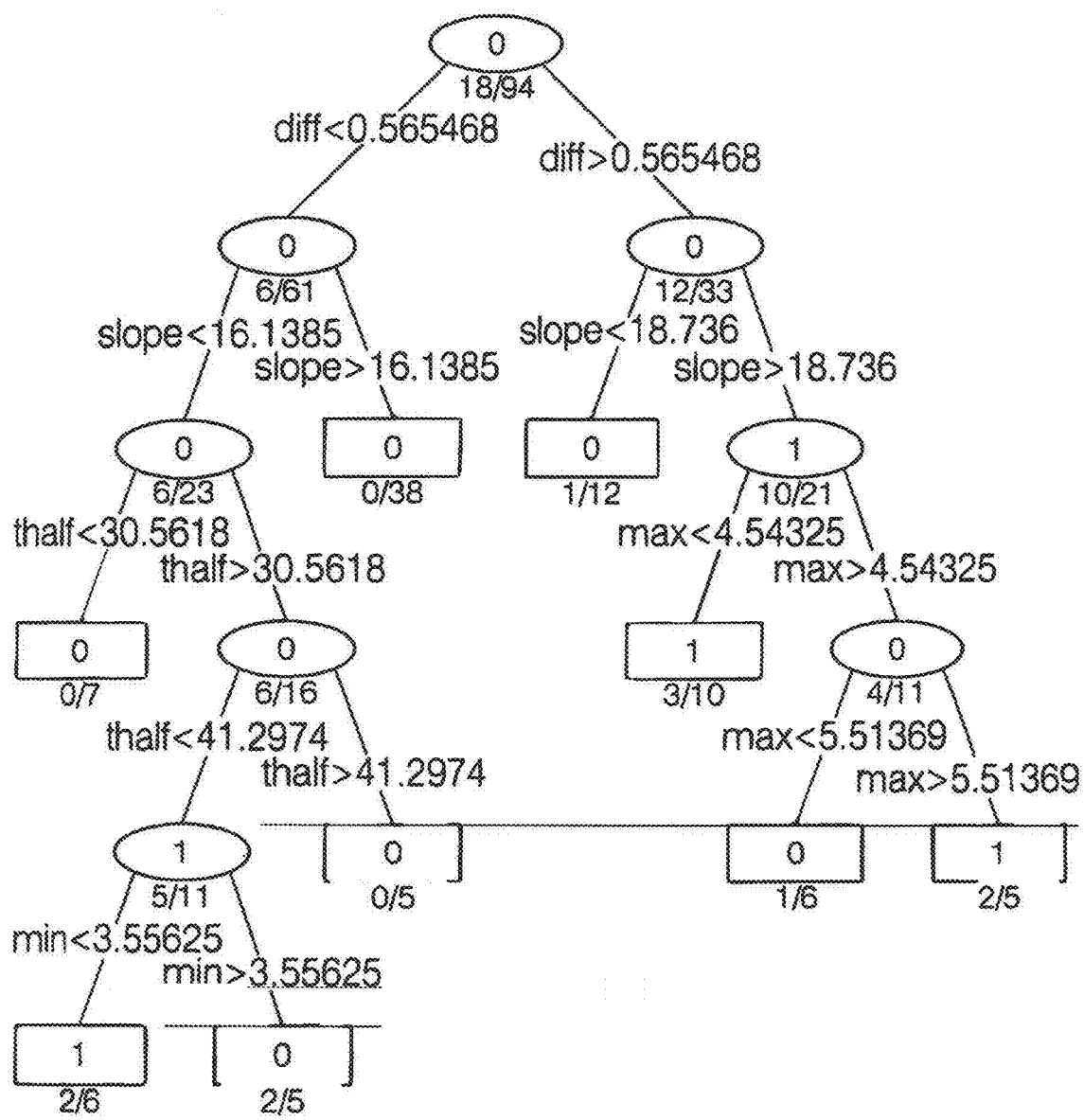
FIG. 2 shows a decisional tree used to calculate the positivity of the method in a patient with total blood PSA below 4 ng/ml.
Figure 3:
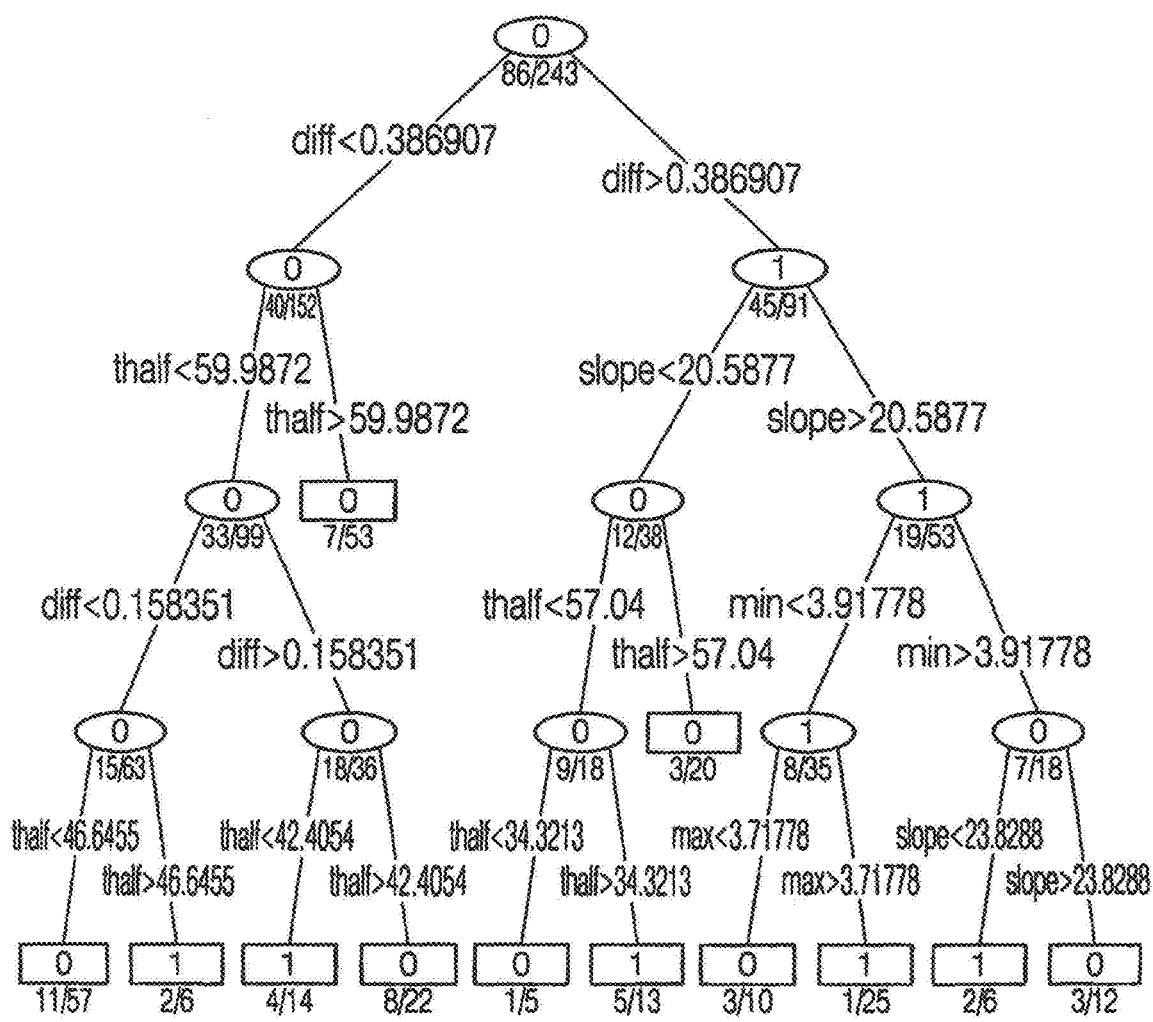
FIG. 3 shows a decisional tree used to calculate the positivity of the method in a patient with total blood PSA between 4-10 ng/ml.
Figure 4:
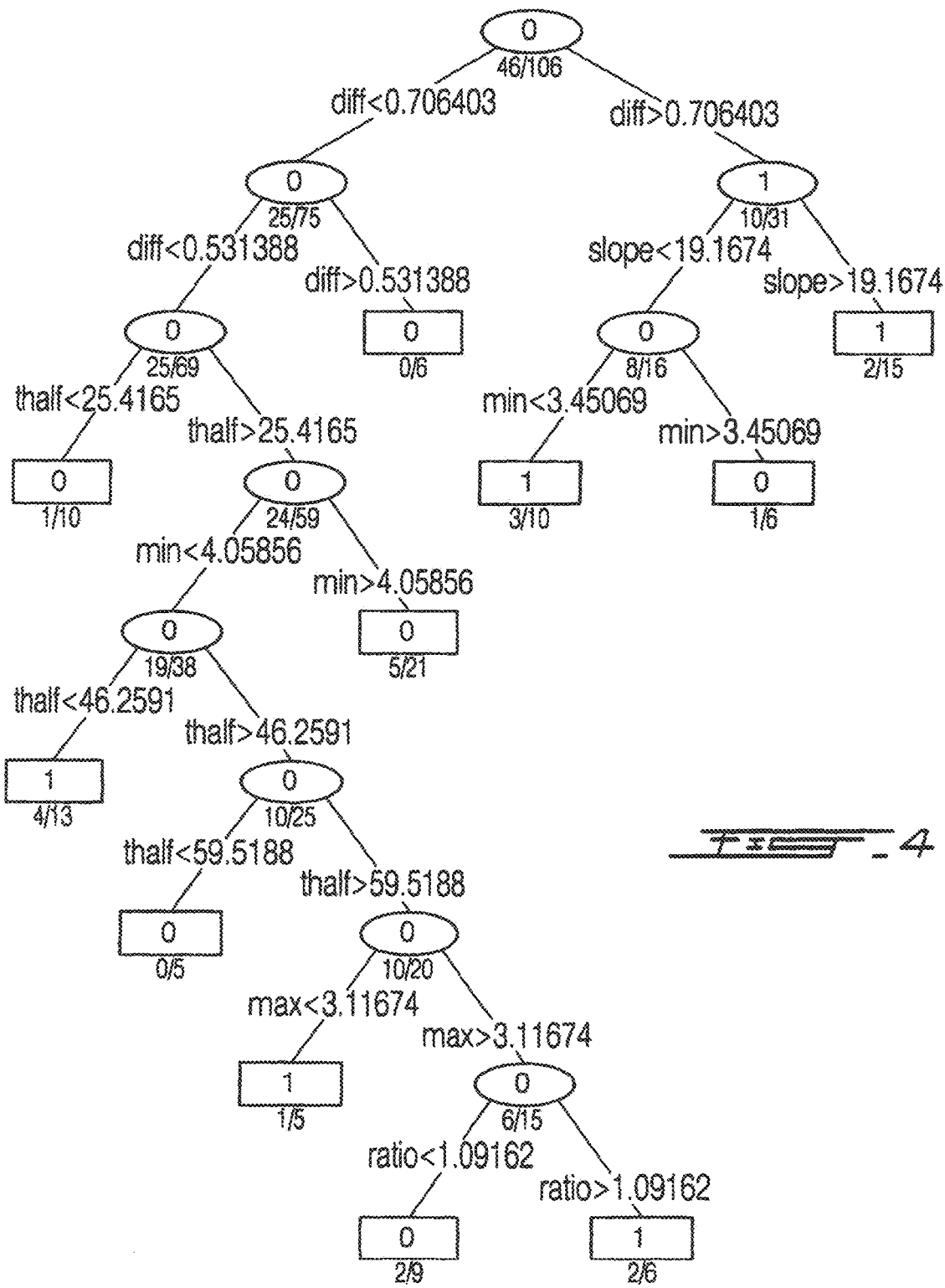
FIG. 4 shows a decisional tree used to calculate the positivity of the method in a patient with total blood PSA above 10 ng/ml.

Clinical specificity (Sp) and sensitivity (Se) of the method has been estimated following a tree-structured classification using S-Plus™ software [Insightful Corporation, Seattle, Wash., USA] starting from raw fluorimeter data. Three structured trees have been defined for the three types of patients defined as having a total blood PSA (tPSA) below 4 ng/ml, between 4-10 ng/ml and above 10 ng/ml (see FIGS. 2-4 and TABLE 4.

TABLE 4

Method sensitivity and specificity

| tPSA | Number | Se % | Sp % |
|---|---|---|---|
| <4 ng/ml | 94 | 74 (14/19) | 91 (68/75) |
| 4-10 ng/ml | 243 | 59 (50/85) | 91 (144/158) |
| >10 ng/ml | 106 | 79 (37/47) | 80 (47/59) |
| Overall | 443 | 67 (101/151) | 89 (259/292) |

TABLE 5

Method performance versus total tPSA and free fPSA

| | Se % | Sp % |
|---|---|---|
| tPSA ≥ 2.5 ng/ml | 100% (58/58) | 6% (5/88) |
| tPSA ≥ 4.0 ng/ml | 88% (51/58) | 15% (13/88) |

TABLE 5-continued

Method performance versus total tPSA and free fPSA

| | Se % | Sp % |
|---|---|---|
| FPSA/tPSA ≤ 0.15 | 72% (42/58) | 56% (49/88) |
| FPSA/tPSA ≤ 0.13 | 66% (38/58) | 67% (59/88) |
| uPM3 ™ | 64% (37/58) | 91% (80/88) |

146/443 patients with available fPSA

The study demonstrated that the method has a positive predictive value (PPV) of 75%, compared to total PSA (>4.0 ng/ml) with a PPV of only 38%. The negative predictive value of the method is 84%, compared to 81% for tPSA. The overall accuracy of the method is 81%, compared with an accuracy of 47% for tPSA.

Although the present invention has been described hereinabove by way of illustrative embodiments thereof, it will be appreciated by one skilled in the art from reading of this disclosure that various changes in form and detail can be made without departing from the spirit and nature of the invention as defined in the appended claims. For example, various other amplification assays or detection assays, different probes and primers sequences as well as slightly different temperature and time of incubation may be used according to the present invention

What is claimed is:

1. A method of characterizing nucleic acids of a urine sample, the method comprising:
   (a) performing a first amplification reaction on nucleic acids of the urine sample using at least a first primer pair to produce a first amplification product, wherein: the first primer pair is specific for a PCA3 RNA or a cDNA prepared therefrom,
   the urine sample comprises at least one prostate cell or nucleic acid extract thereof, and
   the PCA3 RNA:
   (i) comprises the sequence of SEQ ID NO: 9, 10 or 13,
   (ii) hybridizes under high stringency conditions to the RNA of (i), wherein the high stringency conditions comprise a hybridization at 65° C. in 6×SSC or 5×SSPE, 5×Denhardt's solution, 0.5% SDS and 100 µg/ml denatured carrier DNA and a washing at 65° C. in 0.2×SSC/0.1% SDS, or
   (iii) is fully complementary to the RNA of (i) or (ii);
   (b) performing a second amplification reaction on nucleic acids of the urine sample using at least a second primer pair to produce a second amplification product, wherein the second primer pair is specific for a PSA RNA or a cDNA prepared therefrom; and
   (c) detecting levels of the first and the second amplification products produced in the first and second amplification reactions, respectively.

2. The method of claim 1, wherein the urine sample comprises malignant prostate cells or a nucleic acid extract thereof.

3. The method of claim 1, wherein the urine sample comprises crude urine.

4. The method of claim 1, wherein the urine sample comprises the first voided urine following a digital rectal examination.

5. The method of claim 1, comprising simultaneously amplifying the PCA3 RNA or cDNA prepared therefrom and the PSA RNA or cDNA prepared therefrom to produce the first and second amplification products, respectively, in a multiplex reaction.

6. The method of claim 1, comprising performing a nucleic acid amplification which is at least one of:
   (a) real-time amplification;
   (b) nucleic acid sequence-based amplification (NASBA);
   (c) polymerase chain reaction (PCR);
   (d) transcription-mediated amplification assay (TMA); or
   (e) ligase chain reaction.

7. The method of claim 1, comprising detecting levels of the first and second amplification products using fluorescence detection, chemiluminescence detection, or colorimetry detection.

8. The method of claim 1, wherein the first primer pair comprises a promoter-primer suitable for transcription-mediated amplification of the PCA3 RNA or cDNA prepared therefrom.

9. The method of claim 1, wherein the urine sample comprises RNA extracted from crude urine using:
(a) a silica based purification method, or
(b) a target capture method.

10. The method of claim 1, wherein the first amplification product comprises PCA3 exon sequences or the complements thereof, but does not comprise PCA3 intron sequences.

11. The method of claim 10, wherein the first primer pair amplifies sequences from PCA3 exon 3 and exon 4 without amplifying any sequence from an intron therebetween.

12. The method of claim 1, wherein the first amplification reaction is a first isothermal amplification reaction that cannot use genomic DNA as a template to produce the first amplification product.

13. The method of claim 12, wherein the first primer pair amplifies sequences from PCA3 exon 3 and exon 4 without amplifying any sequence from an intron therebetween.

14. The method of claim 13, wherein steps (a) and (c) are carried out simultaneously in a multiplex reaction.

15. The method of claim 14, wherein the urine sample comprises the first voided urine following a digital rectal examination.

16. The method of claim 15, wherein the urine sample comprises malignant prostate cells or a nucleic acid extract thereof.

17. The method of claim 14, wherein step (c) comprises detecting the level of the first amplification product with a first hybridization probe, and detecting the level of the second amplification product with a second hybridization probe, wherein each of the hybridization probes comprises a different fluorophore.

18. The method of claim 1, wherein steps (a) and (c) are carried out simultaneously in a multiplex reaction, and wherein the first and second amplification reactions of the multiplex reaction are first and second transcription mediated amplification reactions.

19. The method of claim 1, wherein the first primer pair comprises oligonucleotides comprising the sequences set forth in SEQ ID NOs: 3 and 4.

20. The method of claim 1, wherein the second primer pair comprises oligonucleotides comprising the sequence set forth in SEQ ID NOs: 1 and 2.

* * * * *